(12) United States Patent
Valdez et al.

(10) Patent No.: US 11,231,424 B2
(45) Date of Patent: *Jan. 25, 2022

(54) LEVETIRACETAM IMMUNOASSAYS

(71) Applicant: ARK Diagnostics, Inc., Fremont, CA (US)

(72) Inventors: Johnny Jose Valdez, Fremont, CA (US); Byung Sook Moon, Palo Alto, CA (US); Ki Chung, Palo Alto, CA (US); Alejandro A. Orozco, Gilroy, CA (US)

(73) Assignee: ARK Diagnostics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/720,886

(22) Filed: Dec. 19, 2019

(65) Prior Publication Data

US 2020/0240991 A1 Jul. 30, 2020

Related U.S. Application Data

(60) Continuation of application No. 14/459,221, filed on Aug. 13, 2014, now abandoned, which is a continuation of application No. 13/427,764, filed on Mar. 22, 2012, now Pat. No. 8,841,136, which is a division of application No. 12/604,249, filed on Oct. 22, 2009, now Pat. No. 8,168,756.

(60) Provisional application No. 61/108,369, filed on Oct. 24, 2008.

(51) Int. Cl.
*G01N 33/58* (2006.01)
*C07K 16/44* (2006.01)
*G01N 33/94* (2006.01)
*C07D 207/26* (2006.01)

(52) U.S. Cl.
CPC ......... *G01N 33/581* (2013.01); *C07D 207/26* (2013.01); *C07K 16/44* (2013.01); *G01N 33/9473* (2013.01); *G01N 2458/00* (2013.01)

(58) Field of Classification Search
CPC .. C07D 207/26; C07K 16/44; G01N 2458/00; G01N 33/581; G01N 33/9473
See application file for complete search history.

(56) References Cited

U.S. PATENT DOCUMENTS

| | | | |
|---|---|---|---|
| 3,817,837 A | 6/1974 | Rubenstein et al. |
| 3,875,011 A | 4/1975 | Rubenstein et al. |
| 4,492,762 A | 1/1985 | Wang et al. |
| 4,708,929 A | 11/1987 | Henderson |
| 4,816,567 A | 3/1989 | Cabilly et al. |
| 4,857,453 A | 9/1989 | Ullman et al. |
| 4,868,131 A | 9/1989 | Hiratsuka |
| 5,851,829 A | 12/1998 | Marasco et al. |
| 5,965,371 A | 10/1999 | Marasco et al. |
| 6,455,288 B1 | 9/2002 | Jakobovits et al. |
| 6,514,770 B1 | 2/2003 | Sorin |
| 6,784,197 B2 | 8/2004 | Differding et al. |
| 7,037,939 B2 | 5/2006 | Hwang et al. |
| 7,101,980 B2 | 9/2006 | Hui et al. |
| 7,169,907 B2 | 1/2007 | Hui |
| 7,183,259 B2 | 2/2007 | Scheueman et al. |
| 7,202,092 B2 | 4/2007 | Ghoshal et al. |
| 7,205,116 B2 | 4/2007 | Salamone et al. |
| 7,271,252 B2 | 9/2007 | Sigler et al. |
| 7,358,276 B2 | 4/2008 | Differding et al. |
| 8,168,756 B2 | 5/2012 | Valdez et al. |
| 8,828,665 B2 | 9/2014 | Valdez et al. |
| 8,841,136 B2 | 9/2014 | Valdez et al. |
| 9,522,880 B2 | 12/2016 | Valdez et al. |
| 9,920,136 B2 | 3/2018 | Valdez et al. |
| 9,970,929 B2 | 5/2018 | Valdez et al. |
| 10,203,345 B2 | 2/2019 | Valdez et al. |
| 2002/0058656 A1 | 5/2002 | Ockert |
| 2002/0098999 A1 | 7/2002 | Gallop et al. |
| 2002/0111338 A1 | 8/2002 | Cundy et al. |
| 2002/0151529 A1 | 10/2002 | Cundy et al. |
| 2003/0158254 A1 | 8/2003 | Zerangue et al. |
| 2003/0181390 A1 | 9/2003 | Gallop et al. |
| 2004/0248811 A1 | 12/2004 | Hwang et al. |
| 2004/0254344 A1 | 12/2004 | Gallop et al. |
| 2005/0148564 A1 | 7/2005 | Cundy et al. |
| 2005/0228035 A1 | 10/2005 | Feuerstein et al. |
| 2005/0244816 A1 | 11/2005 | Valdez |
| 2005/0272710 A1 | 12/2005 | Cundy et al. |
| 2005/0288228 A1 | 12/2005 | Cundy et al. |
| 2006/0115865 A1 | 6/2006 | Ouyang et al. |
| 2006/0141548 A1 | 6/2006 | Roberts et al. |
| 2007/0135356 A1 | 6/2007 | Scheueman et al. |

(Continued)

FOREIGN PATENT DOCUMENTS

EP 0659751 6/1995
EP 1470825 10/2004

(Continued)

OTHER PUBLICATIONS

Chen et al., (1996) "Development of an Enzyme-Linked Immunosorbent Assay for a Broad Spectrum Triazole Fungicide: Hexaconazole" J. Agric. Food Chem 44 1352-1356.
Coachman et al., (2012) "An automated method for the simultaneous measurement of azole antifungal drugs in human plasma or serum using turbulent flow liquid chromatography-tandem mass spectrometry" Anal Bioanal Chem. 404:513-523.
Manclus et al., (2008) "Development of Monoclonal Immunoassays for the Determination of Triazole Fungicides in Fruit Juices," J. Agric. Food Chem. 56: 8793-8800.
Nagappan et al., (2007) "Posaconazole: A Broad-Spectrum Triazole Antifungal Agent" Clinical Infectious Diseases 45(12):1610-1617.
Oh et al., "ARK™ Homogeneous Enzyme Immunoassays for Voriconazole and Posaconazole," posted on Internet on Sep. 19, 2013.

(Continued)

*Primary Examiner* — Galina M. Yakovleva
(74) *Attorney, Agent, or Firm* — Rudy J. Ng; Bozicevic, Field & Francis LLP

(57) ABSTRACT

Methods, compositions and kits are disclosed directed at levetiracetam derivatives, immunogens, signal generating moieties, antibodies that bind levetiracetam and immunoassays for detection of levetiracetam.

11 Claims, 5 Drawing Sheets

(56) References Cited

U.S. PATENT DOCUMENTS

| | | |
|---|---|---|
| 2008/0009018 A1 | 1/2008 | Ouyang et al. |
| 2008/0199887 A1 | 8/2008 | Valdez et al. |
| 2009/0093069 A1 | 4/2009 | Valdez et al. |
| 2010/0173427 A1 | 7/2010 | Valdez et al. |
| 2011/0105448 A1 | 5/2011 | Dhuppad et al. |
| 2011/0212944 A1 | 9/2011 | Lui et al. |
| 2012/0190047 A1 | 7/2012 | Valdez et al. |
| 2014/0206020 A1 | 4/2014 | Valdez et al. |
| 2019/0145991 A1 | 5/2019 | Valdez et al. |

FOREIGN PATENT DOCUMENTS

| | | |
|---|---|---|
| WO | WO 9700248 | 1/1997 |
| WO | WO 9733858 | 9/1997 |
| WO | WO 0050027 | 8/2000 |
| WO | WO 2001062726 | 8/2001 |
| WO | WO 0228883 | 4/2002 |
| WO | WO 0242414 | 5/2002 |
| WO | WO 0300642 | 1/2003 |
| WO | WO 07065036 | 6/2007 |
| WO | WO 2008097640 | 8/2008 |
| WO | WO 2011020605 | 2/2011 |
| WO | WO 2012172015 | 12/2012 |

OTHER PUBLICATIONS

Schiller et al., (2007) "Posaconazole: An extended-spectrum triazole antifungal agent," Clinical Therapeutics, Excerpta Medica Princeton 29(9) 1862-1886.

Sharma & Bhatia (2011) "Triazoles in Antifungal Therapy: A Review" International Journal of Research in Pharmaceutical and Biomedical Science 2(2): 417-427.

Steinmann et al., (2010) "Comparison and evaluation of a novel bioassay and high-performance liquid chromatography for the clinical measurement of serum voriconazole concentration," Mycoses 54(5) e421-e428.

Cendejas-Bueno et al., (2012) "HPLC/UV or Bioassay: Two Valid Methods for Posaconazole Quantification in Human Serum Samples", Clin. Microbiol. Infect. 18(12) 1229-1235.

Englebienne (2000) "Immune and Receptor Assays in Theory and Practice," CRC Press 308.

Goodrow, et al., (1995) "Strategies for Immunoassay Hapten Design," In Immunoanalysis of Agrochemicals, 586(9):119-139.

Howard, et al., (2008) "Clinical application of voriconazole concentrations in the treatment of invasive aspergillosis," Ann. Pharmacother., 42(12): 1859-1864.

Szurdoki et al., (1995) "Important Factors in Hapten Design and Enzyme-Linked Immunosorbent Assay Development," in Immunoanalysis of Agrochemicals: Nelson, J., et al.: ACS Symposium Series, 586(4) 39-63.

Tojo et al., (2006) "Oxidation of primary alchohols to carboxylic acids," Springer 1-114.

U.S. Appl. No. 12/032,528, filed Feb. 15, 2008, issued as U.S. Pat. No. 8,828,665.

U.S. Appl. No. 14/447,179, filed Jul. 30, 2014, issued as U.S. Pat. No. 9,522,880.

U.S. Appl. No. 15/349,832, filed Nov. 11, 2016, issued as U.S. Pat. No. 10,203,345.

U.S. Appl. No. 16/247,255, filed Jan. 14, 2019, published as US 2019/0145991.

U.S. Appl. No. 12/604,249, filed Oct. 22, 2009, issued as U.S. Pat. No. 8,168,756.

U.S. Appl. No. 13/427,764, filed Mar. 22, 2012, issued as U.S. Pat. No. 8,841,136

U.S. Appl. No. 14/158,485, filed Jan. 17, 2014, issued as U.S. Pat. No. 9,970,929.

U.S. Appl. No. 14/176,462, filed Feb. 10, 2014, issued as U.S. Pat. No. 9,920,136.

Engvall "Enzyme immunoassay ELISA and EMIT," *Methods Enzymol* 70:419-439 (1980).

Gunther, et al., "QMS Levetiracetam Assay on the Hitachi 917 System," Clinical Chemistry, 55(6): Supplement, Abstract E-167 (2009).

Hurwitz, et al., "Levetiracetam Induced Interstitial Nephritis and Renal Failure," Pediatr. Neurol, 41:57-58 (2009).

Kohler and Milstein,"Continuous cultures of fused cells secreting antibody of predefined specificity," Nature, 256: 495-497 (1975).

McCafferty, et al., "Phage antibodies: filmentous phage displaying antibody variable domains," *Nature* 348:552-554 (1990).

Roffey, et al., "The Disposition of Voriconazole in Mouse, Rat, Rabbit, Guinea Pig, Dog, and Human" *Drug Metabolism and Disposition*, 31 (6):731-781 (2003).

Contin et al., "Levetiracetam Therapeutic Monitoring in Patients with Epilepsy Effect of Concomitant Antiepileptic Drugs," *Ther Drug Monit.* 26(4): 375-379(2004).

Extended European Search Report for European Application No. 09822719.2, dated Jan. 11, 2012.

Feng et al. "Structural characterization of the oxidative degradation products of an antifungal agent SCH 56592 by LC-NMR and LC-MS." *J. of Pharm and Biom. Analysis* 25 (3-4): 545-557 (2001).

Na, "Synthesis and Activity of Novel 1-Halogenobenzylindole Linked Triazole Derivatives as Antifungal Agents" Bull. Korean Chem Soc. 32(1): 307-310 (2011).

Noyer, et al. "The Novel Antiepileptic Drug Levetiracetam (ucb L059) Appears to Act via a Specific Binding Site in CNS Membranes" *Eur. J. Pharmolcol.* 286(2):137-146 (1995).

Sargentini-Maier, et al., "Pharmacokinetics and Metabolism of 14C-Brivaracetam, a Novel SV2A Ligand, in Healthy Subjects" Drug Metab. Dispos. ,36(1):36-45 (2008).

Urdabayev and Uoyang "Novel Levetiracetam Derivatives for Immunoassay" The 236th ACS National Meeting, Philadelphia, Proposed Activities, August 17-21, Abstract Published Online (2008).

Warrilow, et al., "Identification, Characterization, and Azole-Binding Properties of *Mycobacterium smegmatis* CYP16A2, a Homolog of ML2088 the Sole Cytochrome P450 Gene of *Mycobacterium leprae*" *Antimbrob. Agents Chemother* 56(3): 1157-1164 (2009).

Kenda, et al.; "Discovery of 4-Substituted Pyrrolidone Butanamides as New Agents with Significant Antiepileptic Activity," J. Med. Chem., 47(3):530-535 (2004).

Mayer, et al., "Luminescent Label-More than just an alternative to radioisotopes?" Angewandte Chemie, 33(10), 1044-1072 (1994).

Nolli, et al., "Antibodies against the antibiotics: an overview," *Ann. 1st Super Sanita*, 27(1):149-154 (1991).

Williams, et al., Interlaboratory variability in the quantification of new generation antieoileptic drugs based on External quality assessment data. Epilepsia, 44(1):40-45 (2003).

(1)  (2)

Antibody:
Produced by Levetiracetam derivatve immunogen

Enzyme Conj.
Levetiracetam derivative-G6PDH

Antibody binding to G6PDH Conj. inhibits activit

Structural Formula:

LEVETIRACETAM IMMUNOASSAYS

CROSS REFERENCE TO RELATED APPLICATION

This application is a continuation of U.S. application Ser. No. 14/459,221, filed Aug. 13, 2014, which is a continuation of U.S. application Ser. No. 13/427,764, filed Mar. 22, 2012, now U.S. Pat. No. 8,841,136, which is a divisional of U.S. application Ser. No. 12/604,249, filed Oct. 22, 2009, now U.S. Pat. No. 8,168,756, which claims priority under 35 U.S.C. § 119(e) to U.S. Provisional Patent Application No. 61/108,369 filed Oct. 24, 2008, which are incorporated herein by reference in their entirety and for all purposes.

BACKGROUND

The chemical name of levetiracetam, a single enantiomer, is (−)-(S)-α-ethyl-2-oxo-1-pyrrolidine acetamide, its molecular formula is $C_8H_{14}N_2O_2$ and its molecular weight is 170.21.

Levetiracetam is chemically unrelated to existing antiepileptic drugs (AEDs). It has the following structural formula:

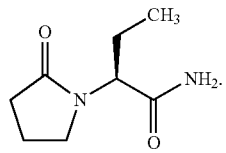

Situations in which AED therapeutic drug monitoring ("TDM") are most likely to be of benefit have been described (*Epilepsia*, 49(7):1239-1276, 2008). They include (1) when a person has attained the desired clinical outcome, to establish an individual therapeutic concentration which can be used at subsequent times to assess potential causes for a change in drug response; (2) as an aid in the diagnosis of clinical toxicity; (3) to assess compliance, particularly in patients with uncontrolled seizures or breakthrough seizures; (4) to guide dosage adjustment in situations associated with increased pharmacokinetic variability (e.g., children, the elderly, patients with associated diseases, drug formulation changes); (5) when a potentially important pharmacokinetic change is anticipated (e.g., in pregnancy, or when an interacting drug is added or removed); and (6) to guide dose adjustments for AEDs with dose-dependent pharmacokinetics.

Therapeutic drug management of levetiracetam would serve as an excellent tool to ensure compliance in administering chemotherapy with the actual prescribed dosage and achievement of the effective serum concentration levels. The role of TDM for levetiracetam may also be useful in managing patients that are overdosed.

To date no anti-levetiracetam antibody has been produced and no commercially available immunoassay has been developed for levetiracetam.

SUMMARY

Figure 1:
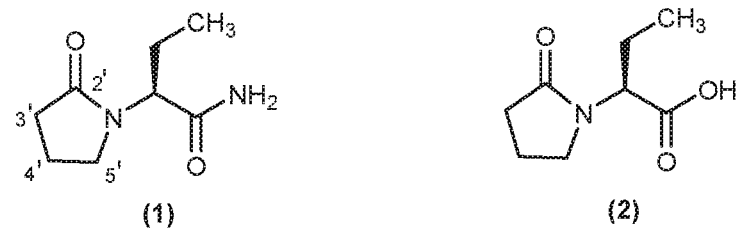
FIG. 1 shows chemical structures: (1) levetiracetam, (2) 2-pyrrolidone-N-butyric acid metabolite.

Methods, compositions and kits are disclosed directed at levetiracetam derivatives, immunogens, signal generating moieties, antibodies that bind levetiracetam and immunoassays for detection of levetiracetam.

The embodiments provide for detection of levetiracetam in a sample. A variety of haptens, hapten-reactive partner conjugates, hapten derivatives, receptors, methods, and kits are useful in this determination.

A certain embodiment is a compound of Formula 1 shown below:

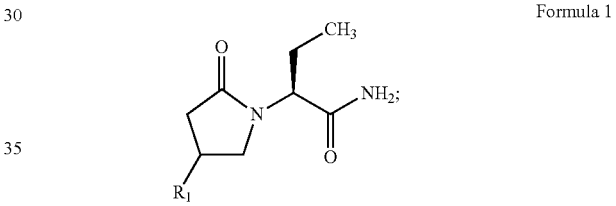

Formula 1 wherein $R_1$ is —Y—Z, and Y is a linking group and Z is selected from the group consisting of hydrogen, —OH, —SH, —S-acyl; —O-lower alkyl, halogen, $NH_2$, -epoxy, -maleimidyl, haloacetamide, carboxyl and all its activated forms including hydroxysuccinimidyl, -succinimidyl, -carbonate, anhydride, imidate, an immunogenic carrier, a protein, and a label, and including acid salts thereof.

A certain embodiment is a compound of Formula 2 shown below:

Formula 2 wherein $R_2$ is —Y—Z, and Y is a linking group and Z is selected from the group consisting of hydrogen, —OH, —SH, —S-acyl; —O-lower alkyl, halogen, $NH_2$, -epoxy, -maleimidyl, haloacetamide, carboxyl and all its activated forms including hydroxysuccinimidyl, -succinimidyl, -carbonate, anhydride, imidate, an immunogenic carrier, a protein, and a label, and including acid salts thereof.

A certain embodiment is a compound of Formula 3 shown below:

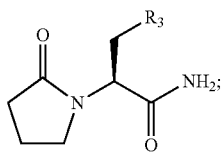

Formula 3 wherein R$_3$ is —Y—Z, and Y is a linking group and Z is selected from the group consisting of hydrogen, —OH, —SH, —S-acyl; —O-lower alkyl, halogen, NH$_2$, -epoxy, -maleimidyl, haloacetamide, carboxyl and all its activated forms including hydroxysuccinimidyl, -succinimidyl, -carbonate, anhydride, imidate, an immunogenic carrier, a protein, and a label, and including acid salts thereof.

The disclosure provides a method for determining a presence of levetiracetam. The method comprises providing in combination in a medium: (a) a sample suspected of containing the compound; and, (b) an antibody raised against a compound of any of the above formulas 1-3. The medium is examined for the presence a complex comprising the compound and the antibody where the presence of such as complex indicates the presence of the compound in the sample. In one aspect of the above embodiment, the combination further comprises a labeled conjugate of the above compound.

A certain embodiment is a kit for determining a presence of levetiracetam. The kit comprises (a) an antibody reactive to a common epitope present in levetiracetam and compounds shown in formulas 1-3; (b) ancillary reagents for determining the compound; and, (c) a labeled conjugate of a compound of any of the above formulas 1-3. The antibody of the kit may be an antibody raised against a compound of any of the formulas 1-3 above.

Definitions

Unless defined otherwise, all technical and scientific terms used herein have the same meaning as commonly understood by one of ordinary skill in the art to which this invention is related. The following terms are defined for purposes of the present disclosure.

Analyte

The compound or composition to be measured, the material of interest such as levetiracetam.

Sample Suspected of Containing Analyte

Any sample which is reasonably suspected of containing analyte can be analyzed by the method of the embodiments. Such samples can include human, animal or man-made samples. The sample can be prepared in any convenient medium which does not interfere with the assay. Typically, the sample is an aqueous solution or a natural fluid, preferably, urine, whole blood, serum, plasma, cerebral-spinal fluid, or saliva more preferably, serum.

Measuring the Amount of Analyte

Quantitative, semiquantitative, and qualitative methods as well as all other methods for determining analyte are considered to be methods of measuring the amount of analyte. For example, a method which merely detects the presence or absence of analyte in a sample suspected of containing an analyte is considered to be included within the scope of the embodiments. Synonyms for the phrase "measuring the amount of analyte" which are contemplated within the scope of the embodiments include, but are not limited to, detecting, measuring, or determining analyte; detecting, measuring, or determining the presence of analyte; and detecting, or determining the amount of analyte.

Human Serum

"Human serum", as used herein, refers to the aqueous portion of human blood remaining after the fibrin and suspended material (such as cells) have been removed.

Immunoassay

As used herein, the terms "immunoassay" or "immunodiagnostic" refer to laboratory techniques or test systems that make use of the binding between an antigen or analyte and an antibody in order to identify and/or quantify at least one of the specific antigen or analyte or specific antibody in a biological sample.

As used here, the term "competitive immunoassay" refers to a experimental protocol in which a known amount of an identifiable antigen or analyte competes with another antigen or analyte for binding with an antibody. That is, a known antigen or analyte that binds with a known antibody is combined with a sample that is suspected of containing another antigen or analyte that also binds with the known antibody. This allows for the known antigen or analyte and another antigen or analyte to both compete for the binding site on the antibody. For example, a levetiracetam derivative that binds with an anti-levetiracetam antibody can be combined with a sample suspected of containing levetiracetam, and the derivative and levetiracetam compete for binding with the anti-levetiracetam antibody. The competition for binding with the antibody can then be used to determine whether or not levetiracetam is present in the sample, and can further be used to quantify the amount of levetiracetam in the sample.

Linking Group

The term "linker" or "linking group" refers to a portion of a chemical structure that connects two or more substructures.

Conjugate

A conjugate is a molecule comprised of two or more substructures bound together, optionally through a linking group, to form a single structure. The binding can be made either by a direct connection (e.g. a chemical bond) between the subunits or by use of a linking group. For example, a conjugate is a G6PDH enzyme or a label protein including alkaline phosphatase, β-galactosidase and horse radish peroxidase or a chemical label such as a fluorescent, luminescent or colorimetric molecule or microparticle attached to a hapten or analyte analog or derivative.

Conjugation

Conjugation is any process wherein two subunits are linked together to form a conjugate. The conjugation process can be comprised of any number of steps.

Derivative

As used herein, a "derivative" is a compound derived or obtained from another and containing essential elements of the parent substance. Thus, in one embodiment, the term derivative refers to a chemical compound or molecule made from levetiracetam by one or more chemical reactions. As such, a derivative can be a compound with a structure similar to that of levetiracetam or based on levetiracetam.

Hapten

Haptens are capable of binding specifically to corresponding antibodies, but usually do not themselves act as immunogens for preparation of the antibodies. Antibodies which recognize a hapten can be prepared against compounds comprised of the hapten linked to an immunogenic carrier.

Antibody

The term "anti-levetiracetam antibody" refers to antibodies that are capable of specifically binding a levetiracetam epitope of levetiracetam, a levetiracetam derivative, or a levetiracetam conjugate. "Anti-levetiracetam antibodies" include both polyclonal and monoclonal antibodies, as well as antigen-binding fragments thereof as defined above. A "levetiracetam epitope" refers to an epitope that is present in levetiracetam and in a levetiracetam derivative (e.g., a levetiracetam conjugate).

The term "binds specifically" or "specifically binds" in the context of antibody binding, refers to high avidity and/or high affinity binding of an antibody to a specific antigen, e.g., to levetiracetam. In specific binding under appropriate conditions, antibody binding to levetiracetam is stronger than binding of the same antibody to any other epitope, particularly those which may be present in molecules in association with, or in the same sample, as the levetiracetam to be detected, e.g., binds more strongly (e.g., higher affinity, higher avidity, or both) to levetiracetam than to a non-levetiracetam epitope so that by adjusting binding conditions the antibody binds almost exclusively to levetiracetam or a levetiracetam moiety as present in a compound of the present disclosure (see Formula 1-3), and not to non-levetiracetam moieties that may be present in the sample. Antibodies which bind specifically to levetiracetam may be capable of binding other antigens at a weak, yet detectable, level (e.g., 10% or less of the binding shown to levetiracetam). Such weak binding, or background binding, is readily discernible from the specific antibody binding to levetiracetam, e.g., by use of appropriate controls. "Antibody activity" or "antibody binding activity" in the context of analyte binding assays generally refers to the ability of an antibody to bind a specific antigen or analyte in preference to other potential antigens or analytes via the antigen combining site located within a variable region of an immunoglobulin.

The term "antibody" includes a protein molecule having one or more polypeptides substantially encoded by all or part of the recognized immunoglobulin genes. The recognized immunoglobulin genes, for example in humans, include the kappa ($\kappa$), lambda ($\kappa$), and heavy chain genetic loci, which together comprise the myriad variable region genes, and the constant region genes mu ($\mu$), delta ($\delta$), gamma ($\gamma$), epsilon ($\epsilon$), and alpha ($\alpha$) which encode the IgM, IgD, IgG, IgE, and IgA isotypes respectively. Antibody herein is meant to include full length antibodies and antibody fragments, and may refer to a natural antibody from any organism, an engineered antibody, or an antibody generated recombinantly for experimental, therapeutic, or other purposes as further defined below. Thus, the term "antibody raised against a compound" includes a synthesized antibody or compound having the same structure as an antibody raised against the compound The term "antibody" includes antibody fragments, as are known in the art, such as Fab, Fab', F(ab')$_2$, Fv, scFv, or other antigen-binding subsequences of antibodies, either produced by the modification of whole antibodies or those synthesized de novo using recombinant DNA technologies. The term "antibody" refers to both monoclonal and polyclonal antibodies. Antibodies can be antagonists, agonists, neutralizing, inhibitory, or stimulatory.

As used herein, the term "polyclonal antibody" refers to a heterogeneous mixture of antibodies with a wide range of specificities and affinities to a given antigen or epitope. Thus, the polyclonal antibody, which can also be referred to as polyclonal antibodies, can include a plurality of antibodies, each distinguishable from the others, that bind or otherwise interact with an antigen. The term "polyclonal" refers to antibodies originating from multiple progenitor cells. The different antibodies that comprise a polyclonal antibody can be produced or generated by injecting an immunogen having an epitope into an animal and, after an appropriate time, collecting and optionally purifying the blood fraction containing the antibodies of interest. In producing antibodies, several parameters can be considered with respect to the final use for the polyclonal antibody. These parameters include the following: (1) the specificity of the antibody (i.e., the ability to distinguish between antigens); (2) the avidity of the antibody (i.e., the strength of binding an epitope); and (3) the titer of the antibody, which determines the optimal dilution of the antibody in the assay system.

As used herein, the term "monoclonal antibody" refers to an antibody that is isolated from a culture of normal antibody-producing cells and one unique progenitor cell. A monoclonal antibody can have a homogeneous binding constant. The monoclonal antibodies include an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies include hybrid and recombinant antibodies produced by splicing a variable (including hypervariable) domain of an anti-inhibitor antibody with a constant domain, or a light chain with a heavy chain, or a chain from one species with a chain from another species, or fusions with heterologous proteins, regardless of species of origin or immunoglobulin class or subclass designation, as well as antibody fragments, e.g., Fab, F(ab)2, and Fv 1, so long as they exhibit the desired biological activity. For example, the monoclonal antibodies may be made by the hybridoma method first described by Kohler & Milstein, Nature, 256:495 (1975), or may be made by recombinant DNA methods (U.S. Pat. No. 4,816,567). The "monoclonal antibodies" may also be isolated from phage libraries generated using the techniques described in, e.g., McCafferty et al., Nature, 348:552-554 (1990).

Antigen

"Antigen", as used herein, refers to a compound that binds specifically to the variable region or binding site of an antibody. The term "antigen" and "immunogen" may in some cases be used interchangeably.

Epitope

The term "epitope" refers to a region of an antigen that interacts with an antibody molecule. An antigenic molecule can have one or more epitopes that can be recognized by the same or different antibodies. An epitope or epitopic moiety may comprise a unique chemical configuration of an antigen, hapten or a reactive ligand. The chemical configuration may be a linear sequence of chemical composition or even a spatial array of chemical groups in the chemical configuration. An epitope is the chemical configuration that associates directly with the binding site in the antibody molecule. The antibody and the chemical group, hapten or reacting ligand containing the epitope form the "specific binding pair."

Immunogen

As used herein, the terms "immunogen" and "immunogenic" are meant to refer to substances capable of producing or generating an immune response (e.g., antibody response) in an organism. An immunogen can also be antigen. In one embodiment, the immunogen has a fairly high molecular weight (e.g. greater than 10,000). Thus, a variety of macromolecules such as proteins, lipoproteins, polysaccharides, nucleic acids and teichoic acids can be coupled to a hapten in order to form an immunogen in accordance with the embodiments.

As used herein, the term "immunogenicity" refers to the ability of a molecule to induce an immune response, which is determined both by the intrinsic chemical structure of the injected molecule and by whether or not the host animal can recognize the compound. Small changes in the structure of an antigen can greatly alter the immunogenicity of a compound and have been used extensively as a general procedure to increase the chances of raising an antibody, particularly against well-conserved antigens. For example, these modification techniques either alter regions of the immunogen to provide better sites for T-Cell binding or expose new epitopes for B-cell binding.

Immunogenic Carrier

"Immunogenic Carrier", "Carrier," or "Immunogenic Moiety," as Used Herein, Refers to any material that when combined with a hapten stimulates an in vitro or in vivo immune response. A hapten becomes an immunogenic moiety when coupled to a carrier and as part of the immunogen can induce an immune response and elicit the production of antibodies that can bind specifically with the hapten. Immunogenic carrier moieties include proteins, peptides (including polypeptides), glycoproteins, saccharides including complex polysaccharides, particles, nucleic acids, polynucleotides, and the like that are recognized as foreign and thereby elicit an immunologic response from the host.

Inhibitory Antibody

An antibody capable of inhibiting the activity of an enzyme or an enzyme-hapten conjugate upon binding an epitope present on the enzyme.

Accuracy

The term "accuracy" refers to the closeness of the agreement between the result of a measurand and a true value of the measurand. The measurand is the substance measured or analyzed, the analyte or the ligand entering the binding reaction with the receptor or antibody.

Specificity

The term "specificity" or "selectivity" refers to the preferential binding of a ligand to a receptor (e.g., antibody). Thus, specificity may refer, in one embodiment, to the degree that levetiracetam is bound selectively by an antibody. One measure of the specificity of a receptor to a ligand is crossreactivity. Compounds that cross-react are referred to as "crossreactants." Crossreactants may occur as the result of the biotransformation of levetiracetam by the human body to a metabolite, such as levetiracetam being biotransformed into 2-pyrrolidone-N-butyric acid. Anti-levetiracetam antibodies of the present disclosure include those that bind an epitope of levetiracetam, but that do not detectably bind a metabolite of levetiracetam, such as a 2-pyrrolidone-N-butyric acid metabolite of levetiracetam.

Levetiracetam Derivative

A "levetiracetam derivative" as used in this disclosure refers to a compound sharing a core structure with levetiracetam and that can compete with levetiracetam for binding to an anti-levetiracetam binding partner, such as an anti-levetiracetam antibody.

Certain compounds disclosed herein in connection with embodiments can exist in unsolvated forms as well as solvated forms, including hydrated forms. In general, the solvated forms are equivalent to unsolvated forms and are encompassed within the reference to the compounds set out in the present disclosure. Certain compounds disclosed herein in connection with embodiments may exist in multiple crystalline or amorphous forms.

Isolated

As used herein, the term "isolated," when used in the context of an isolated compound, antibody, conjugate, etc., refers to a compound of interest (e.g., a compound as described herein, a conjugate as described herein, an antibody as described herein, etc.) that is in an environment different from that in which the compound naturally occurs. "Isolated" is meant to include compounds of interest (e.g., a compound as described herein, a conjugate as described herein, or an antibody as described herein) that are within samples that are substantially enriched for the compound of interest and/or in which the compound of interest is partially or substantially purified. As used herein, the term "substantially pure" refers to a compound of interest that is removed from its natural environment and is at least 60% free, at least about 75% free, at least about 90% free, at least about 95% free, at least about 98% free, or more than 98% free, from other components with which it is naturally associated, and/or with it may be associated during synthesis or production.

Certain compounds disclosed herein in connection with embodiments possess asymmetric carbon atoms (optical centers) or double bonds; the racemates, diastereomers, geometric isomers and individual isomers are encompassed within the scope of the embodiments.

The compounds may be prepared as a single isomer (e.g., enantiomer, cis-trans, positional, diastereomer) or as a mixture of isomers. In one embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), Vogel's Encyclopedia of Practical Organic Chemistry, 5th ed., Longman Scientific and Technical Ltd., Essex, 1991, pp. 809-816; and Heller, Acc. Chem. Res. 23: 128 (1990).

Where substituent groups are specified by their conventional chemical formulae, written from left to right, they equally encompass the chemically identical substituents, which would result from writing the structure from right to left, e.g., —$CH_2O$— is intended to also recite —$OCH_2$—. Use of a single dash ("-") or double dash ("—" or "--") refers to a single covalent bond, while use of "=" refers to a double bond. The symbol, $)_2$ or $_2($, when displayed with —S, indicates that the compound inside the parenthesis may be present as a dimer forming a disulfide bond. The dimer may be reduced to a monomer.

Acyl or Alkanoyl

The term "acyl" or "alkanoyl" by itself or in combination with another term, means, unless otherwise stated, a stable straight or branched chain, or cyclic hydrocarbon radical, or combinations thereof, having the stated number of carbon atoms and an acyl radical on at least one terminus of the alkane radical. The "acyl radical" is the group derived from a carboxylic acid by removing the —OH moiety therefrom.

Alkyl

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl.", where "heteroalkyl" refers to carbon chains having one or more substitutions at one or more carbon atoms of the hydrocarbon chain fragment. Alkyl groups that are limited to hydrocarbon groups are termed "homoalkyl". Certain alkyl groups include those containing between about one and about twenty five carbon atoms (e.g. methyl, ethyl and the like).

Lower Alkyl

The term "lower alkyl" generally refers to a straight, branched, or cyclic hydrocarbon chain containing 8 or fewer carbon atoms, and can contain from 1 to 8, from 1 to 6, or from 1 to 4 carbon atoms. Certain "lower alkyl" groups include methyl, ethyl, n-propyl, isopropyl, n-butyl, sec-butyl, tert-butyl, n-pentyl, n-hexyl, n-heptyl and the like. "Lower alkyls" can be optionally substituted at one or more carbon atoms of the hydrocarbon chain.

Alkoxy, Alkylamino and Alkylthio

The terms "alkoxy," "alkylamino" and "alkylthio" (or thioalkoxy) are used to refer to those alkyl groups attached to the remainder of the molecule via an oxygen atom, an amino group, or a sulfur atom, respectively.

Heteroatom

By "heteroatom" is meant atoms other than a carbon which may be present in a carbon backbone or a linear, branched or cyclic compound. Certain heteroatoms include oxygen (O), nitrogen (N), sulfur (S), phosphorus (P) and silicon (Si). Heteroatoms can be present in their reduced forms, e.g., —OH, —NH, and —SH.

Heteroalkyl

The term "heteroalkyl," by itself or in combination with another term, means, unless otherwise stated, a straight or branched chain, or cyclic carbon-containing radical, or combinations thereof, having the stated number of carbon atoms and at least one heteroatom which can be a member selected from O, N, Si, P and S, wherein the nitrogen, phosphorous and sulfur atoms are optionally oxidized, and the nitrogen heteroatom is optionally be quaternized. Normally heteroalkyl groups contain no more than two heteroatoms linked in sequence. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Generally, up to two heteroatoms may be consecutive, such as, for example, —CH$_2$—NH—OCH$_3$ and —CH$_2$—O—Si(CH$_3$)$_3$.

Heteroalkylene

Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

Cycloalkyl and Heterocycloalkyl

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Aryl

The term "aryl" means, unless otherwise stated, a polyunsaturated, aromatic moiety that can be a single ring or multiple rings (usually from 1 to 3 rings), which are fused together or linked covalently. The term "heteroaryl" refers to aryl groups (or rings) that contain from one to four heteroatoms which are members selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Certain substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" where each can be independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the embodiments includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" can be independently selected from hydrogen, substituted or unsubstituted alkyl, substituted or unsubstituted heteroalkyl, substituted or unsubstituted aryl and substituted or unsubstituted heteroaryl. When a compound of the embodiments includes more than one R group, for example, each of the R groups is independently selected as are each R', R", R"' and R"" groups when more than one of these groups is present. In the schemes that follow, the symbol X represents "R" as described above.

Amino and Amine Group

The term "amino" or "amine group" refers to the group —NR'R" (or N$^+$RR'R") where R, R' and R" are independently selected from hydrogen, alkyl, substituted alkyl, aryl, substituted aryl, aryl alkyl, substituted aryl alkyl, heteroaryl, and substituted heteroaryl. A substituted amine is an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

Polypeptide

"Polypeptide" as used herein is meant to encompass a polyaminoacid of any length, and encompasses proteins, protein fragments and peptides. Polypeptides may be genetically encoded or synthetically produced. Polypeptides may also be modified, e.g., by post-translational and/or chemical modification(s).

Detectable Label

As used herein, a "detectable label" generally refers to an identifying tag that can provide for a detectable signal, e.g., luminescence (e.g., photoluminescence (e.g., fluorescence, phosphorescence), chemoluminescence (e.g., bioluminescence), microparticle aggregation or formation, radioactivity, immunodetection, enzymatic activity, and the like.

Detectably Labeled Antibody

By "detectably labeled antibody" an antibody (which, as defined above, includes antigen-binding fragments, etc.) having an attached detectable label. The detectable label may be attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies to detect an antigen are well known in the art.

Antibody-Analyte Complex and Antibody-Antigen Complex

"Antibody-analyte complex", "antibody-antigen complex" generally refers to a complex that results following specific binding of an antibody and its antigen or analyte, e.g., between an anti-levetiracetam antibody and levetiracetam (or a levetiracetam derivative, e.g., levetiracetam conjugate).

Assessing

The term "assessing" includes any form of measurement, and includes determining the presence or absence if an element. The terms "assessing", "determining" (e.g., as in "determining the presence or absence of"), "measuring", "evaluating", and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

DETAILED DESCRIPTION OF EMBODIMENTS

Before embodiments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the embodiments. The upper and lower limits of these smaller ranges may independently be included or excluded in the range, and each range where either, neither or both limits are included in the smaller ranges is also encompassed within the embodiments, subject to any specifically excluded limit in the stated range. Where the stated range includes one or both of the limits, ranges excluding either or both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can be used in the practice or testing of the embodiments, some methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a conjugate" includes a plurality of such conjugates and reference to "the sample" includes reference to one or more samples and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Immuno Assay

Currently, there are three classes of immunoassay, which are described as follows: (1) antibody capture assays; (2) antigen capture assays; and (3) two-antibody sandwich assays. Additionally, it is contemplated that new immunoassays will be developed and will be capable of employing the hapten derivatives and antibodies that form the specific binding pair of the embodiments. Immunoassay or immunodiagnostic test systems measure a ligand or target analyte, the measurand (e.g., levetiracetam), by using the selective binding properties of an antibody and a signal generating system comprising a signal generating moiety that is responsive or reactive to the presence of antibody due to the binding of the antibody with hapten conjugated to the signal generating moiety.

Homogeneous enzyme immunoassays depend on the availability of enzyme-hapten conjugates whose enzyme activity can be strongly modulated upon binding of an antibody raised against an epitope present on the hapten. In one aspect, the embodiments provide enzyme-hapten conjugates and antibodies for conducting assays that are useful in homogeneous immunoassays. "Homogeneous immunoassay", as used herein, refers to an assay method where the complex is typically in solution and not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents (U.S. Pat. Nos. 3,996,345; 4,161,515; 4,256,834 and 4,264,968); enzyme and enzyme inhibitor pairs on different reagents (U.S. Pat. Nos. 4,208,479 and 4,233,401); chromophore and chromophore modifier pairs on different reagents (U.S. Pat. No. 4,208,479); and latex agglutination assays (U.S. Pat. Nos. 3,088,875; 3,551,555; 4,205,954 and 4,351,824).

The anti-levetiracetam antibodies, either monoclonal or polyclonal, can be used in immunoassays for identifying the presence of levetiracetam in a biological sample, such as blood, plasma, serum, urine, tissue, and the like. This can be beneficial for identifying or determining pharmacokinetic and/or pharmacodynamic parameters for levetiracetam in a patient or patient population. Thus, the anti-levetiracetam antibodies can be used in immunodiagnostic assays so that the assays can be configured for identifying the presence and optionally quantifying the amount of levetiracetam. Additionally, the immunodiagnostic assays can use levetiracetam derivatives in accordance with embodiments.

Levetiracetam Derivatives

A certain embodiment is a compound of Formula 1 shown below:

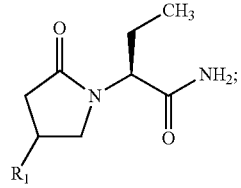

Formula 1 wherein $R_1$ is —Y—Z, and Y is a linking group and Z is selected from the group consisting of hydrogen, —OH, —SH, —S-acyl; —O-lower alkyl, halogen, —$NH_2$, -epoxy, -maleimidyl, haloacetamide, carboxyl, activated carboxyl, an immunogenic carrier, a protein, and a label, and including acid salts thereof. Activated carboxyl includes all activated forms of carboxyl including, but not limited to, hydroxysuccinimidyl, succinimidyl, carbonate, and anhydride.

In certain embodiments, in Formula 1, Z is selected from the group consisting of hydrogen, —OH, —SH, —S-acyl; —O-lower alkyl, halogen, $NH_2$, -epoxy, -maleimidyl, haloacetamide, carboxyl, and activated carboxyl. In certain embodiments, Z is selected from the group consisting of —SH, halogen, $NH_2$, -maleimidyl, carboxyl, and activated carboxyl. In certain embodiments, Z is halogen. In certain embodiments, Z is bromo. In certain embodiments, Z is carboxyl. In certain embodiments, Z is —$NH_2$. In certain embodiments, Z is —SH.

In certain embodiments, in Formula 1, Z is an immunogenic carrier. Examples of immunogenetic carriers include proteins, peptides, glycoproteins, saccharides, particles, nucleic acids, and polynucleotides. In certain embodiments, Z is an immunogenic carrier selected from hemocyanins, globulins, albumins, and polysaccharides. Examples of certain immunogenic carrier include keyhole limpet hemocyanin (KLH), bovine serum albumin (BSA), or human serum albumin (HSA). In certain embodiments, Z is an immunogenic carrier selected from BSA and KLH.

In certain embodiments, in Formula 1, Z is a protein. Examples of certain proteins that are also immunogenic carriers include keyhole limpet hemocyanin (KLH), bovine serum albumin (BSA), or human serum albumin (HSA).

In certain embodiments, in Formula 1, Z is a label. Examples of labels for Z include, but are not limited to, isotopic labels and non-isotopic signal generating moieties. Examples of non-isotopic signal generating moieties include fluorophores and enzymes, which are described in further detail below.

Certain fluorophores include, but are not limited to, naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate), rhodamine derivatives (e.g. rhodamine isothiocyanate), phycoerythin, and Texas Red.

Certain enzymes include, but are not limited to, alkaline phosphatase, horseradish peroxidase, lysozyme, glucose-6-phosphate dehydrogenase, lactate dehydrogenase, β-galactosidase, and urease. Also, a genetically engineered fragment of an enzyme may be used, such as the donor and acceptor fragment of β-galactosidase utilized in CEDIA immunoassays. In a certain embodiment, the enzyme is glucose-6-phosphate dehydrogenase (G6PDH), alkaline phosphatase, β-galactosidase, and horseradish peroxidase. In a certain embodiment, the enzyme is glucose-6-phosphate dehydrogenase (G6PDH).

In certain embodiments, in Formula 1, Z is a halogen, such as bromo; and Y is a linker comprising 3 carbon atoms and one nitrogen atom. In certain embodiments, Formula 1 is a compound of the formula:

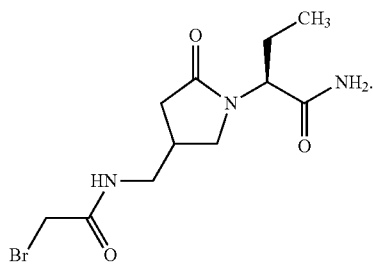 [SMILES: CC[C@@H](C(N)=O)N1CC(CNC(=O)CBr)CC1=O]

In certain embodiments, in Formula 1, Z is a halogen, such as bromo; and Y is a linker comprising 4-5 carbon atoms and one nitrogen atom. In certain embodiments, Formula 1 is a compound of the formula:

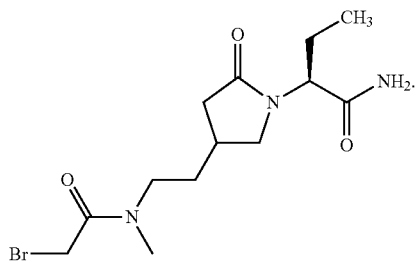 [SMILES: CC[C@@H](C(N)=O)N1CC(CCN(C)C(=O)CBr)CC1=O]

In certain embodiments, in Formula 1, Z is selected from the group consisting of —SH, halogen, $NH_2$, -maleimidyl, carboxyl, and activated carboxyl; and Y is a linker comprising 1-5 carbon atoms and zero or one nitrogen atom. In certain embodiments, in Formula 1, Z is selected from the group consisting of —SH, halogen, $NH_2$, -maleimidyl, carboxyl, and activated carboxyl; and Y is —$(CH_2)_n$-C(O)NH—$(CH_2)_n$-, where each n is an integer from one to ten. In certain embodiments, in Formula 1, Z is selected from the group consisting of —SH, halogen, $NH_2$, -maleimidyl, carboxyl, and activated carboxyl; and Y is —$(CH_2)_n$-C(O)NH—$(CH_2)_n$-, where each n is one or two. In certain embodiments, in Formula 1, Z is selected from the group consisting of —SH, halogen, $NH_2$, -maleimidyl, carboxyl, and activated carboxyl; and Y is —$(CH_2)_n$-, where n is an integer from one to ten. In certain embodiments, in Formula 1, Z is selected from the group consisting of —SH, halogen, $NH_2$, -maleimidyl, carboxyl, and activated carboxyl; and Y is —$(CH_2)$—.

A certain embodiment is a compound of Formula 2 shown below:

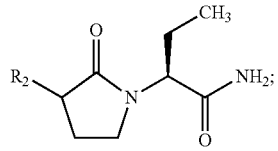

Formula 2 wherein $R_2$ is —Y—Z, and Y is a linking group and Z is selected from the group consisting of hydrogen, —OH, —SH, —S-acyl; —O-lower alkyl, halogen, —$NH_2$, -epoxy, -maleimidyl, haloacetamide, carboxyl, activated carboxyl, an immunogenic carrier, a protein, and a label, and including acid salts thereof. Activated carboxyl includes all activated forms of carboxyl including, but not limited to, hydroxysuccinimidyl, succinimidyl, carbonate, and anhydride.

In certain embodiments, in Formula 2, Z is selected from the group consisting of hydrogen, —OH, —SH, —S-acyl; —O-lower alkyl, halogen, $NH_2$, -epoxy, -maleimidyl, haloacetamide, carboxyl, and activated carboxyl. In certain embodiments, Z is selected from the group consisting of —SH, halogen, $NH_2$, -maleimidyl, carboxyl, and activated carboxyl. In certain embodiments, Z is halogen. In certain embodiments, Z is bromo. In certain embodiments, Z is carboxyl. In certain embodiments, Z is —$NH_2$. In certain embodiments, Z is —SH.

In certain embodiments, in Formula 2, Z is an immunogenic carrier. Examples of immunogenetic carriers include proteins, peptides, glycoproteins, saccharides, particles, nucleic acids, and polynucleotides. In certain embodiments, Z is an immunogenic carrier selected from hemocyanins, globulins, albumins, and polysaccharides. Examples of certain immunogenic carrier include keyhole limpet hemocyanin (KLH), bovine serum albumin (BSA), or human serum albumin (HSA). In certain embodiments, Z is an immunogenic carrier selected from BSA and KLH.

In certain embodiments, in Formula 2, Z is a protein. Examples of certain proteins that are also immunogenic carriers include keyhole limpet hemocyanin (KLH), bovine serum albumin (BSA), or human serum albumin (HSA).

In certain embodiments, in Formula 2, Z is a label. Examples of labels for Z include, but are not limited to, isotopic labels and non-isotopic signal generating moieties. Examples of non-isotopic signal generating moieties include fluorophores and enzymes, which are described in further detail below.

Certain fluorophores include, but are not limited to, naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate), rhodamine derivatives (e.g. rhodamine isothiocyanate), phycoerythin, and Texas Red.

Certain enzymes include, but are not limited to, alkaline phosphatase, horseradish peroxidase, lysozyme, glucose-6-phosphate dehydrogenase, lactate dehydrogenase, β-galactosidase, and urease. Also, a genetically engineered fragment of an enzyme may be used, such as the donor and acceptor fragment of β-galactosidase utilized in CEDIA immunoassays. In a certain embodiment, the enzyme is glucose-6-phosphate dehydrogenase (G6PDH), alkaline phosphatase, β-galactosidase, and horseradish peroxidase. In a certain embodiment, the enzyme is glucose-6-phosphate dehydrogenase (G6PDH).

In certain embodiments, in Formula 2, Z is selected from the group consisting of —SH, halogen, $NH_2$, -maleimidyl, carboxyl, and activated carboxyl; and Y is a linker comprising 1-5 carbon atoms and zero or one nitrogen atom. In certain embodiments, in Formula 1, Z is selected from the group consisting of —SH, halogen, $NH_2$, -maleimidyl, carboxyl, and activated carboxyl; and Y is —$(CH_2)$n-C(O)NH—$(CH_2)$n-, where each n is an integer from one to ten. In certain embodiments, in Formula 1, Z is selected from the group consisting of —SH, halogen, $NH_2$, -maleimidyl, carboxyl, and activated carboxyl; and Y is —$(CH_2)$n-C(O)NH—$(CH_2)$n-, where each n is one or two. In certain embodiments, in Formula 1, Z is selected from the group consisting of —SH, halogen, $NH_2$, -maleimidyl, carboxyl, and activated carboxyl; and Y is —$(CH_2)$n-, where n is an integer from one to ten. In certain embodiments, in Formula 1, Z is selected from the group consisting of —SH, halogen, $NH_2$, -maleimidyl, carboxyl, and activated carboxyl; and Y is —$(CH_2)$—.

A certain embodiment is a compound of Formula 3 shown below:

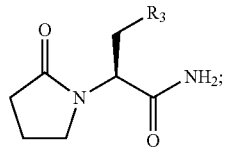

Formula 3 wherein $R_3$ is —Y—Z, and Y is a linking group and Z is selected from the group consisting of hydrogen, —OH, —SH, —S-acyl; —O-lower alkyl, halogen, —$NH_2$, -epoxy, -maleimidyl, haloacetamide, carboxyl, activated carboxyl, an immunogenic carrier, a protein, and a label, and including acid salts thereof. Activated carboxyl includes all activated forms of carboxyl including, but not limited to, hydroxysuccinimidyl, succinimidyl, carbonate, and anhydride.

In certain embodiments, in Formula 3, Z is selected from the group consisting of hydrogen, —OH, —SH, —S-acyl; —O-lower alkyl, halogen, $NH_2$, -epoxy, -maleimidyl, haloacetamide, carboxyl, and activated carboxyl. In certain embodiments, Z is selected from the group consisting of —SH, halogen, $NH_2$, -maleimidyl, carboxyl, and activated carboxyl. In certain embodiments, Z is halogen. In certain embodiments, Z is bromo. In certain embodiments, Z is carboxyl. In certain embodiments, Z is —$NH_2$. In certain embodiments, Z is —SH.

In certain embodiments, in Formula 3, Z is an immunogenic carrier. Examples of immunogenetic carriers include proteins, peptides, glycoproteins, saccharides, particles, nucleic acids, and polynucleotides. In certain embodiments, Z is an immunogenic carrier selected from hemocyanins, globulins, albumins, and polysaccharides. Examples of certain immunogenic carrier include keyhole limpet hemocyanin (KLH), bovine serum albumin (BSA), or human serum albumin (HSA). In certain embodiments, Z is an immunogenic carrier selected from BSA and KLH.

In certain embodiments, in Formula 3, Z is a protein. Examples of certain proteins that are also immunogenic carriers include keyhole limpet hemocyanin (KLH), bovine serum albumin (BSA), or human serum albumin (HSA).

In certain embodiments, in Formula 3, Z is a label. Examples of labels for Z include, but are not limited to, isotopic labels and non-isotopic signal generating moieties. Examples of non-isotopic signal generating moieties include fluorophores and enzymes, which are described in further detail below.

Certain fluorophores include, but are not limited to, naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate), rhodamine derivatives (e.g. rhodamine isothiocyanate), phycoerythin, and Texas Red.

Certain enzymes include, but are not limited to, alkaline phosphatase, horseradish peroxidase, lysozyme, glucose-6-phosphate dehydrogenase, lactate dehydrogenase, β-galactosidase, and urease. Also, a genetically engineered fragment of an enzyme may be used, such as the donor and acceptor fragment of β-galactosidase utilized in CEDIA immunoassays. In a certain embodiment, the enzyme is glucose-6-phosphate dehydrogenase (G6PDH), alkaline phosphatase, β-galactosidase, and horseradish peroxidase. In a certain embodiment, the enzyme is glucose-6-phosphate dehydrogenase (G6PDH).

In certain embodiments, in Formula 3, Z is selected from the group consisting of —SH, halogen, $NH_2$, -maleimidyl, carboxyl, and activated carboxyl; and Y is a linker comprising 1-5 carbon atoms and zero or one nitrogen atom. In certain embodiments, in Formula 1, Z is selected from the group consisting of —SH, halogen, $NH_2$, -maleimidyl, carboxyl, and activated carboxyl; and Y is —$(CH_2)$n-C(O)NH—$(CH_2)$n-, where each n is an integer from one to ten. In certain embodiments, in Formula 1, Z is selected from the group consisting of —SH, halogen, $NH_2$, -maleimidyl, carboxyl, and activated carboxyl; and Y is —$(CH_2)$n-C(O)NH—$(CH_2)$n-, wherein each n is one or two. In certain embodiments, in Formula 1, Z is selected from the group consisting of —SH, halogen, $NH_2$, -maleimidyl, carboxyl, and activated carboxyl; and Y is —$(CH_2)$n-, where n is an integer from one to ten. In certain embodiments, in Formula 1, Z is selected from the group consisting of —SH, halogen, $NH_2$, -maleimidyl, carboxyl, and activated carboxyl; and Y is —$(CH_2)$—.

Linking Group

A linking group or linker has at least 1 uninterrupted chain of atoms extending between the substructures, as depicted as Y in Formulae 1-3. The atoms of a linking group are themselves connected by chemical bonds. The number of atoms in a linking group is determined by counting the atoms other than hydrogen. In some embodiments, the linker is a part of the compound of the embodiments. In some embodiments, the linker can provide a connection between, for example, the levetiracetam derivative of Formula 1 and Z; the levetiracetam derivative of Formula 2 and Z; and the levetiracetam derivative of Formula 3 and Z.

The compounds may be connected to other species by bonding between a reactive functional group on the compound or a linker attached to the compound, and a reactive functional group of complementary reactivity on the other species. A linker may be, for example, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl and combinations thereof. A linker may also include cyclic and/or aromatic groups as part of the chain or as a substitution on one of the atoms in the chain. In one embodiment, the linker may be used to provide an available site on a hapten for conjugating the hapten with, for example, a label, carrier, immunogenic carrier or the like. The linker molecule may be used to connect (conjugate or couple) the ligand, hapten, epitope or epitopic moiety to its immunogenic carrier or signal generating moiety and to display the ligand, hapten, epitope or epitopic moiety for binding to the receptor or antibody. The length of the linker may be varied by those skilled in the art to accomplish the desired outcome in producing the immunogen or the signal generating system.

In certain embodiments, the linking group comprises 1-15 carbon atoms and/or 0-6 heteroatoms. In certain embodiments, the linking group is selected from the group consisting of —$(CH_2)_n$-C(O)—, or —C(O)$(CH_2)_n$- or —C(O)$(CH_2)_n$-NHC(O)—, or —C(O)$(CH_2)_n$-NHC(O)$(CH_2)_n$-, or —$(CH_2)_n$SCH$_2$C(O)—, or —$(CH_2)_n$-C(O)NH—$(CH_2)_n$-, or —$(CH_2)_n$-NH—C(O)—, or —$(CH_2)_n$-NH—C(O)—$(CH_2)_n$-, or —C(O)—$(CH_2)_n$-, or —$(CH_2)_n$-NH—; and n is an integer from 1 to 10, and including acid salts thereof.

In certain embodiments, the linking group is —$(CH_2)_n$-C(O)NH—$(CH_2)_n$-, where each n is an integer from one to ten. In certain embodiments, the linking group is —$(CH_2)_n$-C(O)NH—$(CH_2)_n$-, where each n is one or two. In certain embodiments, the linking group is —$(CH_2)_n$-, where n is an integer from one to ten. In certain embodiments, the linking group is —$(CH_2)_n$—.

In certain embodiments, the linking group is —$(CH_2)_n$-C(O)N$(CH_2)_n(CH_3)$—$(CH_2)_n$-, where each n is an integer from one to ten. In certain embodiments, the linking group is —$(CH_2)_n$-C(O)N$(CH_2)_n(CH_3)$—$(CH_2)_n$-, where each n is one or two.

In certain embodiments, the linking group is —$(CH_2)_n$-C(O)N$(CH_3)$—$(CH_2)_n$-, where each n is an integer from one to ten. In certain embodiments, the linking group is —$(CH_2)_n$-C(O)N$(CH_3)$—$(CH_2)_n$, where each n is one or two.

In certain embodiments, the linking group comprises 10-15 carbon atoms and/or 0-6 heteroatoms.

Additionally, linkers that link a carrier to a hapten can comprise modified or unmodified nucleotides, nucleosides, polymers, sugars and other carbohydrates, polyethers, such as for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. An example of an operative group and its linker is cholesterol-TEG-phosphoramidite, wherein the cholesterol is the operative group and the tetraethylene glycol and phosphate serve as linkers.

In one embodiment, the immunogenic carrier is a protein. Protein carriers can be highly soluble and include functional groups that could facilitate easy conjugation with a hapten molecule. In a certain embodiment, the immunogenic carrier is a member selected from keyhole limpet hemocyanin (KLH), bovine serum albumin (BSA) and human serum albumin (HSA). Keyhole limpet hemocyanin is an oxygen-carrying protein of the marine keyhole limpet, is extremely large and exhibits increased immunogenicity when it is disassociated into subunits. BSA is a highly soluble protein containing numerous functional groups suitable for conjugation.

Derivatives

Derivatives of levetiracetam in accordance with some embodiments can be used to compete for binding with a receptor including an antibody that recognizes both the derivative and levetiracetam. Also, a derivative can include an operative group coupled to levetiracetam through a linker. Thus, the embodiments provide for levetiracetam derivatives linked to, for example, an immunogenic carrier and/or a signal generating moiety as operative groups.

Signal Producing System

The signal producing system is utilized in assays for analytes and may have one or more components, at least one component being a mutant G6PDH. The signal producing system generates a signal that relates to the presence or amount of analyte in a sample. The signal producing system includes all of the reagents required to produce a measurable signal. In one aspect, the G6PDH or a label protein including alkaline phosphatase, B-galactosidase and horse radish peroxidase is conjugated to a sbp member analogous to the analyte.

Other components of the signal producing system can include substrates, enhancers, activators, chemiluminescent compounds, cofactors, inhibitors, scavengers, metal ions, specific binding substances required for binding of signal generating substances, coenzymes, substances that react with enzymic products, other enzymes and catalysts, and the like.

The signal producing system provides a signal detectable by external means, normally by measurement of electromagnetic radiation, desirably by visual examination. For the most part, the signal producing system may include a chromophoric substrate and mutant G6PDH enzyme, where chromophoric substrates are enzymatically converted to dyes which absorb light in the ultraviolet or visible region.

Substantial Change in Enzyme Activity

A change in activity of an enzyme sufficient to allow detection of an analyte when the enzyme is used as a label in an assay for the analyte. Typically, the enzyme's activity is reduced 10-100% preferably 20-99%, more preferably 30-95%.

Ancillary Materials

Various ancillary materials will frequently be employed in an assay in accordance with the embodiments. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Anti-Levetiracetam Antibodies

As noted above, the term "antibody" as used in the context of the present disclosure, refers to a specific binding partner of an analyte (e.g., levetiracetam), and is meant to encompass whole antibodies as well as antigen-binding fragments thereof (such as, for example, F(ab')2, Fab', Fab and Fv), naturally occurring antibodies, hybrid antibodies, chimeric antibodies, single-chain antibodies, and antibody fragments that retain antigen binding specificity, and the like. Antibodies can be of any class (e.g., IgM, IgG, IgA, IgE; frequently IgG) and generated from any source (although usually non-human, usually a non-human mammal such as a rabbit, mouse, rat, goat, etc.). Thus, "antibody" is meant to encompass not only intact immunoglobulin molecules, but also such fragments and derivatives of immunoglobulin molecules as may be prepared by techniques known in the art, and retaining the antibody activity of an intact immunoglobulin.

Antibodies may be derived from polyclonal compositions monoclonal compositions. As noted above, "antibodies" is also meant to encompass single chain antibodies or scFvs, where such recombinantly produced antibody fragments retain the binding characteristics of the above antibodies. Recombinantly produced antibody fragments within the meaning of "antibody" generally include at least the VH and VL domains of the subject antibodies, so as to retain the binding characteristics of the subject antibodies. These recombinantly produced antibody fragments may be readily prepared using any convenient methodology, such as the methodology disclosed in U.S. Pat. Nos. 5,851,829 and 5,965,371; the disclosures of which are herein incorporated by reference.

Anti-levetiracetam antibodies include those that bind one or more levetiracetam epitopes. Anti-levetiracetam antibodies may bind one or more of unconjugated levetiracetam, a levetiracetam derivative, a levetiracetam conjugate, or any combination thereof. The disclosure encompasses an antibody reactive to a common epitope present in levetiracetam and compounds shown in formulas 1-3. Such antibodies can thus bind a levetiracetam epitope as present in levetiracetam and a levetiracetam moiety as present in a compound of any one of Formulae 1 to 3.

Producing Anti-Levetiracetam Antibodies

Anti-levetiracetam antibodies can be prepared by using an immunogenic levetiracetam conjugate described herein and applying methods for antibody production that are well known in the art. For examples of general techniques used in raising, purifying and modifying antibodies, and the design and execution of immunoassays, the reader is referred to Handbook of Experimental Immunology (D. M. Weir & C. C. Blackwell, eds.); Current Protocols in Immunology (J. E. Coligan et al., eds., 1991); David Wild, ed., The Immunoassay Handbook (Stockton Press N.Y., 1994); and R. Masseyeff, W. H. Albert, and N. A. Staines, eds., Methods of Immunological Analysis (Weinheim: VCH Verlags gesellschaft mbH, 1993).

Antibodies obtained using any of the disclosed techniques are screened or purified not only for their ability to react with levetiracetam, but for a low cross-reactivity with potential interfering substances. "Cross-reactivity" may be determined in a quantitative immunoassay by establishing a standard curve using known dilutions of the target analyte, levetiracetam. The standard curve is then used to calculate the apparent concentration of the interfering substance present in various known amounts in samples assayed under similar condition. The cross-reactivity can be calculated as the apparent concentration divided by the actual concentration multiplied by 100. A certain immunoassay for determining cross-reactivity is a homogeneous enzyme immunoassay using a wild type G6PDH as described in U.S. Pat. No. 3,817,837 or mutant G6PDH engineered to contain a cysteine per subunit as described in U.S. Pat. Nos. 6,033,890, 6,090,567 and 6,455,288. Furthermore, the cross-reactivity can be determined in the same type of immunoassay in which the antibody will ultimately be used.

Producing Polyclonal Antibodies

Polyclonal antibodies that bind levetiracetam may be raised by administration of an immunogenic levetiracetam conjugate to an animal host, usually mixed with an adjuvant. Any animal host which produces antibodies can be used. The immunogen is conveniently prepared for injection by rehydrating lyophilized immunogen to form a solution or suspension. Certain adjuvants are water-in-oil immersions, particularly Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of anti-levetiracetam antibody using a levetiracetam-protein conjugate or other levetiracetam conjugates in a standard immunoassay or precipitation reaction.

Methods for purifying specific antibodies having a desired binding specificity from a polyclonal antiserum are known in the art. A particularly effective method is affinity purification using a column of levetiracetam conjugated to a solid phase. One manner of preparing a levetiracetam column is to conjugate levetiracetam or a levetiracetam derivative to a protein other than the protein used in the immunogen, and then attach the conjugate to a commercially available activated resin, such as CNBr-activated SEPHAROSE™. The anti-levetiracetam antibody is passed over the column, the column is washed, and the antibody is eluted with a mild denaturing buffer such as 0.1 M glycine, 0.2 M NaCl, pH 2.5.

Producing Monoclonal Antibodies

Anti-levetiracetam monoclonal antibodies are prepared by a number of different techniques known in the art. For example, for hybridoma technology, the reader is referred generally to Harrow E, Lane D., 1988, *Antibodies, A Laboratory Manual*, Cold Spring Harbor, N.Y.: Cold Spring Harbor Laboratory Press, and Methods in Enzymology, 73B:3 (1981). One common way to produce monoclonal antibodies is to immortalize and clone a splenocyte or other antibody-producing cell recovered from an animal that has been immunized against levetiracetam as described earlier. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing may be performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody may be tested for activity as raw supernatant or ascites, and is optionally purified using standard biochemical preparation techniques such as ammonium sulfate precipitation, ion exchange chromatography, and gel filtration chromatography.

Producing Fragments and other Derivatives of Immunoglobulins

Fragments and other derivatives of immunoglobulins can be prepared by methods of standard protein chemistry, for example, subjecting the antibody to cleavage with a proteolytic enzyme such as pepsin, papain, or trypsin; and reducing disulfide bonds with such reagents as dithiothreitol. Genetically, engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

Detectably Labeled Anti-Levetiracetam Antibodies

The anti-levetiracetam antibodies may also be labeled in order to facilitate detection. A variety of protein labeling schemes are known in the art and may be employed, the particular scheme and label chosen being the one most convenient for the intended use of the antibody, e.g. immunoassay.

Examples of labels include labels that permit both the direct and indirect measurement of the presence of the antibody. Examples of labels that permit direct measurement of the antibody include radiolabels, such as $^3$H or $^{125}$I, fluorescers, dyes, microparticles, beads, chemiluminescers, colloidal particles, and the like. Examples of labels which permit indirect measurement of the presence of the antibody include enzymes where a substrate may provide for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that is conjugated to the enzyme, e.g. the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Immunoassays

The present disclosure provides immunoassay methods for assessing the presence or absence of levetiracetam in a sample of interest. Due to various factors, including the pronounced inter-individual variability in levetiracetam pharmacokinetics, immunoassays to assess levetiracetam status are of interest. Since levetiracetam is excreted renally unchanged and is not metabolized or at least does not produce detectable metabolites. Therefore, there are no pharmacogenomic issues that affect levetiracetam concentration and it is not subject to significant pharmacokinetic drug interactions with other drugs.

Immunoassays of the present disclosure can be of a variety of formats. The immunoassays may be separation immunoassays (also known as heterogeneous immunoassays) or homogeneous immunoassays. Furthermore, the immunoassays may be qualitative or quantitative. Assays of this disclosure include both sandwich and competition assays. The immunoassays may embody assays that are neither sandwich nor competition assays, as in certain assays involving immunoprecipitation.

In general, the immunoassays of the present disclosure for detecting the presence or absence of levetiracetam in a sample can be conducted by adding, to a reaction mixture, (i) a sample suspected of containing levetiracetam and (ii) an anti-levetiracetam antibody capable of forming a complex of levetiracetam that may be present in the sample and the antibody; and detecting the presence or absence of the complex. The presence or absence of said complex is indicative of the presence or absence of levetiracetam in said sample. Moreover, the amount of complex formed can be assessed to determine the concentration of levetiracetam present in the sample (e.g., to provide an assessment of serum or tissue concentration of levetiracetam in a subject from whom the sample was obtained). The presence and/or amount of complex can be assessed directly (e.g., by detecting bound antibody in the complex) or indirectly (e.g., by assessing activity of an enzyme in a levetiracetam enzyme conjugate, where when the levetiracetam enzyme conjugate is not bound to antibody, a detectable signal is generated, indicating that the anti-levetiracetam antibody in the reaction mixture has been bound by levetiracetam from the sample).

In general, the immunoassays of the disclosure entail combining the sample with an anti-levetiracetam antibody under conditions that permit the formation of a stable complex between the analyte to be tested and the antibody.

Assays may be performed in solution or may use a solid (insoluble) support (e.g. polystyrene, nitrocellulose, or beads), using any standard methods (e.g., as described in Current Protocols in Immunology, Coligan et al., ed.; John Wiley & Sons, New York, 1992). Typical methods include ELISAs (enzyme-linked immunosorbent assays), IRMAs (immunoradiometric assays), and RIAs (radioimmunoassays).

Where the assay is performed in solution, the test sample (and, optionally a control sample) is incubated with an anti-levetiracetam antibody for a time period sufficient to allow formation of analyte and affinity reagent complexes, for example, between about 0.1 hrs up to 24 hrs, or more. As previously noted, the anti-levetiracetam antibody may include a detectable label (e.g. radionuclide, fluorescer, or enzyme). The sample is then treated to separate the levetiracetam-anti-levetiracetam antibody complexes from excess, unreacted anti-levetiracetam antibody (e.g. by addition of an anti-anti-levetiracetam antibody (e.g., anti-immunoglobulin antiserum) followed by centrifugation to precipitate the complexes, or by binding to an affinity surface such as a second, unlabelled anti-levetiracetam antibody fixed to a solid substrate such as Sepharose® or a plastic well). Detection of anti-levetiracetam antibody bound to a levetiracetam may be achieved in a variety of ways well known in the art. If necessary, a substrate for the detectable label may be added to the sample.

Where the assay uses a solid support, the support can have an anti-levetiracetam antibody (or levetiracetam conjugate) bound to a support surface. Binding of the assay reagent facilitates the stable, wash-resistant binding of levetiracetam which may be present in the sample (or anti-levetiracetam antibody that is not bound to levetiracetam from the sample, and is present in the reaction mixture, as in a competitive binding assay) to the solid support via specific binding to the anti-levetiracetam antibody. The insoluble supports may be any compositions to which antibodies or suitable levetiracetam conjugates can be bound, which is readily separated from soluble material, and which is otherwise compatible with the overall method of detection of anti-levetiracetam antibody a sample.

The surface of such supports may be solid or porous and of any convenient shape. Examples of suitable insoluble supports to which the anti-levetiracetam antibody is bound include beads, e.g. magnetic beads, membranes and microtiter plates. These can be composed of glass, plastic (e.g. polystyrene), polysaccharides, nylon or nitrocellulose.

Assay reagents can include the anti-levetiracetam antibodies as disclosed herein, as well as anti-anti-levetiracetam antibodies, which may be optionally detectably labeled. Methods for binding antibodies or other proteins to solid supports are well known in the art. After binding of an assay reagent to the support, the support may be treated with a blocking agent, which binds to the support in areas not occupied by the assay reagent Suitable blocking agents include non-interfering proteins such as bovine serum albumin, casein, gelatin, and the like. Alternatively, several detergents at non-interfering concentrations, such as Tween, NP40, TX100, and the like may be used. Such blocking treatment reduces nonspecific binding.

Qualitative and Quantitative Methods

Assays of this disclosure include both qualitative and quantitative assays. Typical quantitative methods involve mixing an analyte with a pre-determined amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise stated, the act of "measuring" or "determining" in this disclosure refers alternately to qualitative and quantitative determination.

Samples

Samples may be biological samples taken from subjects suspected of being administered levetiracetam.

As used herein, a "biological sample" refers to a sample of tissue or fluid isolated from a subject, which in the context of the embodiments generally refers to samples suspected of containing levetiracetam, which samples, after optional processing, can be analyzed in an in vitro assay. Certain samples of interest include, but are not necessarily limited to, a "blood sample" (which as used herein is meant to include whole blood, plasma, serum, and the like), fecal matter, urine, tears, sweat saliva, milk, organs, biopsies, secretions of the intestinal and respiratory tracts, vitreous humor, and fluids obtainable during autopsy (such as cerebrospinal fluid). It should be noted that a "blood-derived sample" refers to a sample that is prepared from blood or a fraction thereof, e.g., plasma or serum. Respiratory secretions (e.g., samples obtained from fluids or tissue of nasal passages, lung, and the like), "Human serum", as used herein, refers to the aqueous portion of human blood remaining after the fibrin and suspended material (such as cells) have been depleted.

Blood samples, such as serum samples, can be obtained by any suitable method. In one embodiment, a trough serum/plasma is used and the concentration range is 12-20 mg. Sweat samples can be obtained using, for example, a PharmChek® sweat patch from Sudormed. The PharmChek® sweat patch includes a semi-occlusive dressing containing a medical grade cellulose blotter paper collection pad, covered by a thin layer of polyurethane and acrylate adhesives. At the end of the wear period, the pad is eluted with a suitable buffer, such as 2.5 mL of 0.2 M acetate buffer with methanol at pH 5.0 (25:75) or with acetonitrile. Furthermore, the biological samples may also be tissue samples, which are extracted into liquid medium for immunoassay. For example, hair samples can be tested by extracting into a liquid medium. The samples may be diluted or modified to facilitate the assay.

The samples may be experimental samples generated by any chemical or biological method. For example, the samples may be standards containing known concentrations of levetiracetam or other substances used for assay calibration.

In some embodiments, the biological sample will be diluted in a suitable solution prior to assaying. In general, a solution suitable for diluting a biological sample will include a buffer, such as phosphate buffered saline (PBS), and may include additional items, such as for example, a non-specific blocking agent, such as bovine serum albumin (BSA), a detergent, such as Triton-X-100, and the like.

Where desired, appropriate control samples for the assay include blood, serum, or urine collected from human subjects who have not received levetiracetam (i.e., a negative control), or samples which contain a known, predetermined amount of a levetiracetam analyte (i.e., a positive control). Alternatively, test results can be compared to detectable signal levels known to be associated with the presence or absence of levetiracetam and/or correlated with an amount of levetiracetam, e.g., a serum level of levetiracetam.

The assays may optionally include use of a calibration standard. "Calibration standard", as used herein, refers to an aqueous medium containing levetiracetam at a predetermined concentration. In a certain embodiment, a series of these calibration standards are available at a series of pre-determined concentrations. In a certain embodiment, the calibration standard is stable at ambient temperature. In a certain embodiment, the calibration standards are in a synthetic matrix. In a certain embodiment, the calibration standards are in a non-synthetic matrix such as human serum.

In many embodiments, a suitable initial source for the human sample is a blood sample. As such, the sample employed in the subject assays is generally a blood-derived sample. The blood derived sample may be derived form whole blood or a fraction thereof, e.g., serum, plasma, etc., where in some embodiments the sample is derived from blood allowed to clot and the serum separated and collected to be used to assay.

In embodiments in which the sample is a serum or serum derived sample, the sample is generally a fluid sample. Any convenient methodology for producing a fluid serum sample may be employed. In many embodiments, the method employs drawing venous blood by skin puncture (e.g., finger stick, venipuncture) into a clotting or serum separator tube, allowing the blood to clot, and centrifuging the serum away from the clotted blood. The serum is then collected and stored until assayed. Once the patient derived sample is obtained, the sample is assayed to determine the level of levetiracetam analyte.

Immunoassay Reagents

Immunoassay reagents that find use alone or in combination in the assays described herein include anti-levetiracetam antibodies, levetiracetam conjugates, and levetiracetam (e.g., as a control or in competitive binding assays). Immunoassay reagents can be provided in a buffered aqueous solution. Such solutions may include additional components such as surface active additives, organic solvents, defoamers, buffers, surfactants, and anti-microbial agents. Surface active additives are introduced to maintain hydrophobic or low-solubility compounds in solution, and stabilize components in the solution. Examples include bulking agents such as betalactoglobulin (BLG) or polyethyleneglycol (PEG); defoamers and surfactants such as Tween-20, Plurafac A38, Triton X-100, Pluronic 25R2, rabbit serum albumin (RSA), bovine serum albumin (BSA), and carbohydrates. Examples of organic solvents can include methanol and other alcohols. Various buffers may be used to maintain the pH of the solution during storage. Illustrative buffers include HEPES, borate, phosphate, carbonate, tris, barbital and the like. Anti-microbial agents also extend the storage life of the immunoassay reagent.

Anti-Levetiracetam Antibodies

Immunoassays generally involve at least one anti-levetiracetam antibody, which may be produced by the methods disclosed herein. In an embodiment, the assays involve using an antibody raised against a levetiracetam derivative-protein conjugate, particularly a low cross-reactivity with non-levetiracetam molecules (i.e., molecules that are not levetiracetam or contain a levetiracetam moiety, such as present in a compound of the present disclosure, see, e.g., the compounds of Formulae 1-3) that may be present in a reaction mixture. Anti-levetiracetam antibodies can be polyclonal or monoclonal, more commonly monoclonal, antibodies, capable of specifically binding levetiracetam.

Depending upon the assay format, the anti-levetiracetam antibody can be optionally detectably labeled, may be used in conjunction with a secondary antibody (i.e., an antibody that specifically binds an anti-levetiracetam antibody) that may be detectably labeled. Certain detectable labels for antibodies are described infra.

Levetiracetam Conjugates

Levetiracetam conjugates variously find use as immunoassay reagents depending on the assay format. For example, levetiracetam conjugate can act as based on competitive binding reagent in competitive binding assays, or can provide for a detectable signal when not bound by an anti-levetiracetam antibody (e.g., where the levetiracetam conjugate is a levetiracetam G6PDH conjugate). Certain levetiracetam conjugates useful as immunoassay reagents are described below.

Detectable Labels

A variety of detectably labels can be used in connection with the levetiracetam conjugate assay reagents for use in the methods disclosed herein. Such detectable labels can be isotopic labels. In other embodiments, the detectable labels are non-isotopic signal-generating moieties, such as fluorophores and enzymes. Certain detectable labels are described below. It will be apparent that while the detectable labels are described below in the context of their use in levetiracetam conjugates, many can also be adapted for use with anti-levetiracetam antibodies.

Fluorophores

"Fluorophore" as used herein refers to moiety that itself fluoresces, can be made to fluoresce, or can provide for quenching of fluorescence of a fluorophore of a FRET pair (e.g., as in a FRET pair). In principle, any fluorophore can be used in the assays of the embodiments. In general, the fluorophore is selected so as to be compatible for use in the assay format desired, and selected so as to be relatively insensitive to the assay conditions, e.g., pH, polarity, temperature and ionic strength.

Certain fluorophores can be characterized as having the following characteristics: a. A fluorescence lifetime of greater than about 15 nsec; b. An excitation wavelength of greater than about 350 nm; c. A Stokes shift (a shift to lower wave-length of the emission relative to absorption) of greater than about 20 nm; d. For homogeneous assays described below, fluorescence lifetime should vary with binding status; and e. The absorptivity and quantum yield of the fluorophore should be high. The longer lifetime is advantageous because it is easier to measure and more easily distinguishable from the Raleigh scattering (background). Excitation wavelengths greater than 350 nm reduce background interference because most fluorescent substances responsible for background fluorescence in biological samples are excited below 350 nm. A greater Stokes shift also allows for less background interference.

The fluorophores generally have a functional group available for conjugation either directly or indirectly to a levetiracetam intermediate to generate a levetiracetam conjugate having the attached fluorophore.

Fluorophores for use in heterogeneous assays can be relatively insensitive to binding status. In contrast, fluorophores for use in homogeneous assay can be sensitive to binding status, i.e., the fluorescence lifetime must be alterable by binding so that bound and free forms can be distinguished.

Examples of fluorophores are naphthalene derivatives (e.g. dansyl chloride), anthracene derivatives (e.g. N-hydroxysuccinimide ester of anthracene propionate), pyrene derivatives (e.g. N-hydroxysuccinimide ester of pyrene butyrate), fluorescein derivatives (e.g. fluorescein isothiocyanate), rhodamine derivatives (e.g. rhodamine isothiocyanate), phycoerythin, and Texas Red.

Enzymes

In a certain embodiment, the signal-generating moiety is an enzyme. From the standpoint of operability, a very wide variety of enzymes can be used. But, as a practical matter, some enzymes have characteristics which make them more readily adaptable to the methods disclosed herein.

The enzyme can be selected so as to be stable to provide for desirable shelf-life, e.g., stable when stored for a period of at least three months or at least six months at temperatures which are convenient to store in the laboratory, normally $-20°$ C. or above. The enzyme can be selected so as to have a satisfactory turnover rate at or near the pH optimum for binding to the antibody, this is normally at about pH 6-10, usually 6.0 to 8.0. A product of the enzymatic reaction facilitated by the enzyme can be either formed or destroyed as a result of the enzyme reaction, and can provide a enzyme reaction product which absorbs light in the ultraviolet region or the visible region, that is the range of about 250-750 nm., usually 300-600 nm. The enzyme may also have a substrate (including cofactors) which has a molecular weight in excess of 300, or in excess of 500. The enzyme which is employed or other enzymes, with like activity, will not be present in the sample to be measured, or can be easily removed or deactivated prior to the addition of the assay reagents. Also, the enzyme can be selected so as to avoid the impact of any naturally occurring inhibitors for the enzyme that may be present in samples to be assayed or as some other component of the reaction mixture.

Although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

It may be desirable to select an enzyme that is susceptible to detectable labeling. In this instance, the enzyme can be detectable labeled using appropriate detectable labels exemplified herein. Certain enzymes include, but are not limited to: alkaline phosphatase, horseradish peroxidase, lysozyme, glucose-6-phosphate dehydrogenase, lactate dehydrogenase, β-galactosidase, and urease. Also, a genetically engineered fragment of an enzyme may be used, such as the donor and acceptor fragment of β-galactosidase utilized in CEDIA immunoassays (see, e.g., Henderson D R et al. Clin Chem. 32(9):1637-1641 (1986)); U.S. Pat. No. 4,708,929. These and other enzymes which can be used have been discussed in detail by Eva Engvall in Enzyme Immunoassay ELISA and EMIT in Methods in Enzymology, 70:419-439 (1980) and in U.S. Pat. No. 4,857,453.

In a certain embodiment, the enzyme is glucose-6-phosphate dehydrogenase (G6PDH) and it is attached to a levetiracetam derivative, thus forming a levetiracetam-reactive partner conjugate.

An anti-levetiracetam antibody used in conjunction with such levetiracetam conjugates can be selected so as to specifically bind the levetiracetam epitope presented by the levetiracetam enzyme conjugate, and thus affect activity of the levetiracetam enzyme conjugate.

For assays employing levetiracetam-enzyme conjugates, as a certain protein conjugate, in which a levetiracetam derivative is labeled with an enzyme, the levetiracetam derivative can be attached to the enzyme by any suitable method. In certain embodiments, the chemistry described herein for formation of immunogenic protein conjugates of levetiracetam derivatives is also used to prepare the enzyme conjugate. In this way, the levetiracetam moiety presented to the antibody can more mirror the levetiracetam epitope to which the antibody specifically binds.

The selection procedure is exemplified using a levetiracetam-reactive partner conjugate comprising G6PDH as the reactive partner and a levetiracetam derivative as the hapten. The first step in selecting an antibody involves testing the magnitude of antibody inhibition of a levetiracetam-reactive partner conjugate. In this step, the goal is to determine and select for those antibodies which significantly inhibit the enzyme activity of G6PDH. Antibodies which perform well in the first test are then subjected to a second test. Here, the antibody is first incubated with levetiracetam. Next the levetiracetam-reactive partner conjugate is added. A certain antibody preferentially binds to levetiracetam instead of the levetiracetam-reactive partner conjugate. The reduction in binding to the levetiracetam-reactive partner conjugate would be visible as an increase G6PDH activity.

Detection

Via Fluorescence

When a fluorescently labeled analyte (i.e., levetiracetam antigen or antibody) is employed, the fluorescence emitted is proportional (either directly or inversely) to the amount of analyte. The amount of fluorescence is determined by the amplitude of the fluorescence decay curve for the fluorescent species. This amplitude parameter is directly proportional to the amount of fluorescent species and accordingly to the analyte.

In general spectroscopic measurement of fluorescence is accomplished by: a. exciting the fluorophore with a pulse of light; b. detecting and storing an image of the excitation pulse and an image of all the fluorescence (the fluorescent transient) induced by the excitation pulse; c. digitizing the image; d. calculating the true fluorescent transient from the digitized data; e. determining the amplitude of the fluorescent transient as an indication of the amount of fluorescent species.

According to the method, substantially all of the fluorescence emitted by the fluorescent species reaching the detector as a function of time from the instant of excitation is measured. As a consequence, the signal being detected is a superimposition of several component signals (for example, background and one analyte specific signal). As mentioned, the individual contributions to the overall fluorescence reaching the detector are distinguished based on the different fluorescence decay rates (lifetimes) of signal components. In order to quantitate the magnitude of each contribution, the detected signal data is processed to obtain the amplitude of each component. The amplitude of each component signal is proportional to the concentration of the fluorescent species.

Via Enzyme

Detection of the amount of product produced by the levetiracetam-reactive partner conjugate of the embodiments can be accomplished by several methods which are known to those of skill in the art. Among these methods are colorimetry, fluorescence, and spectrophotometry. These methods of detection are discussed in "Analytical Biochemistry" by David Holme, Addison-Wesley, 1998, which is incorporated herein by reference.

Solid Supports

The levetiracetam conjugates and/or the anti-levetiracetam antibodies to be used as reagents in an assay can be insolubilized by attachment to a solid phase. This can be, for example, a wall of a vessel containing the reagent, to a particulate, or to a large molecular weight carrier that can be kept in suspension but is removable by physicochemical means, such as centrifugation or microfiltration. The attachment need not be covalent, but is at least of sufficient permanence to withstand any separation techniques (including washes) that are part of the assay procedure. Certain particulate materials include agarose, polystyrene, cellulose, polyacrylamide, latex particles, magnetic particles, and fixed red cells. Examples of commercially available matrices include Sepharose® (Pharmacia), Poros® resins (Roche Molecular Biochemicals), Actigel Superflow™ resins (Sterogene Bioseparations Inc.), and Dynabeads™ (Dynal Inc.). The choice is not critical, and will generally depend on such features as stability, capacity, accessibility of the coupled antibody, flow rate (or the ability to disperse the resin in the reaction mixture), and ease of separation.

Assay Formats

As noted above, immunoassays for detection of levetiracetam can be of a variety of formats, In general, the immunoassays involve combining one or more immunoassay reagents (e.g., at least a anti-levetiracetam antibody) with a test sample (i.e., a sample suspected of containing levetiracetam) in a reaction mixture. "Reaction mixture" generally refers to the combination of a sample suspected of containing levetiracetam and one or more immunoassay reagents as exemplified in the present disclosure to facilitate detection of the presence or absence of levetiracetam in the sample, where the detection may be qualitative or quantitative. The reaction mixture is usually an aqueous solution, although the immunoassay reagent(s) may be in solution or immobilized on a support (e.g., a substrate such as a bead). The reaction mixture can include other components compatible with the immunoassay, e.g., buffers, and the like.

Immunoassays usually are classified in one of several ways. For example, immunoassays can be classified according to the mode of detection used, i.e., enzyme immunoassays, radio immunoassays, fluorescence polarization immunoassays, chemiluminescence immunoassays, turbidimetric assays, etc. Another grouping method is according to the assay procedure used, i.e., competitive assay formats, sandwich-type assay formats as well as assays based on precipitation or agglutination principles. In the instant application, a further distinction is made depending on whether washing steps are included in the procedure (so-called heterogeneous assays) or whether reaction and detection are performed without a washing step (so-called homogeneous assays). Certain assays are described in more detail below.

Homogeneous and Heterogeneous Immunoassays

Immunoassays may be described as heterogeneous or homogeneous. "Homogeneous immunoassay", as used herein, refers to an assay method where the complex is typically not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents; enzyme and enzyme inhibitor pairs on different reagents; chromophore and chromophore modifier pairs on different reagents; and latex agglutination assays.

A certain homogeneous assay is the quantitative homogeneous enzyme immunoassay in which a levetiracetam moiety is conjugated to an active enzyme. The conjugation is arranged so that the binding of an anti-levetiracetam antibody to the derivative affects enzymatic activity in a qualitative or quantitative fashion. If a sample containing levetiracetam is premixed with the antibody, the antibody will complex with the levetiracetam and be prevented from binding to the enzyme conjugate. In this way, the activity of the enzyme can be correlated with the amount of levetiracetam present in the sample.

G6PDH is a certain enzyme useful in such assays. In one embodiment, the G6PDH is a variant of a naturally-occurring G6PDH in which one or more lysine residues are deleted or substituted, or one or more cysteine residues introduced. For example, *Leuconostoc mesenteroides* G6PDH are dimeric enzymes that have the ability to catalyze the oxidation of D-glucose-6-phosphate to D-glucono-delta-lactone-6-phosphate by utilizing either $NAD^+$ or $NADP^+$. This property of using $NAD^+$ differentiates these enzymes from human G6PDH, which utilizes only $NADP^+$ effectively, and allows *L. mesenteroides*-specific G6PDH activity to be measured in the presence of human G6PDH, as for example in human samples. G6PDHs from *L. mesenteroides* are used in current EMIT™ homogeneous immunoassays (Syva Company, Palo Alto, Calif., U.S.A.). Two certain genera of bacteria from which to select G6PDH are *Leuconostoc* and *Zymomonas*. Within these genera *L. mesenteroides, L. citreum, L. lactis, L. dextranicum*, and *Z. mobilis* are of most interest, *L. mesenteroides, L. citreum, L. lactis* are specific examples.

Another example of a homogeneous assay system is the cloned enzyme donor immunoassay.

In a separation-based or "heterogeneous" assay, the detecting of a complex of an anti-levetiracetam antibody and an analyte involves a process wherein the complex formed is physically separated from either unreacted analyte, unreacted antibody, or both.

In a heterogeneous immunoassay, a complex of an anti-levetiracetam antibody and an analyte may be first formed in the fluid phase, and then subsequently captured by a solid phase reagent or separated on the basis of an altered physical or chemical property, such as by gel filtration or precipitation. Alternatively, one of the reagents may be attached to a solid phase before contacting with other reagents, and then the complex may be recovered by washing the solid phase free of unreacted reagents. Separation-based assays typically involve use of a labeled derivative or antibody to facilitate detection or quantitation of the complex. Suitable labels include radioisotopes such as $^{125}I$, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted.

Sandwich and Competition Assays

Assays of this disclosure include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. Competition assays involve a system in which the analyte to be measured competes with an derivative of the analyte for binding to another reagent, such as an antibody. An example of a competition assay using EMIT® is described in U.S. Pat. No. 3,817,837.

In one embodiment, the immunoassay further comprises adding a levetiracetam conjugate comprising a levetiracetam moiety and a detectable label to the sample. The presence or absence of levetiracetam in the sample can be detected by detecting the datable label. The detectable label may comprise an enzyme and the detecting is by assaying activity of the enzyme. In an embodiment, the enzyme is a dehydrogenase, more particularly, G6PDH.

Lateral Flow Chromatography

The compounds and methods of the embodiments also encompass the use of these materials in lateral flow chromatography technologies. The essence of lateral flow chromatography involves a membrane strip which comprises a detection device, such as a non-isotopic signal generating moiety, for levetiracetam. A sample from a patient is then applied to the membrane strip. The sample interacts with the detection device, producing a result. The results can signify several things, including the absence of the levetiracetam in the sample, the presence of the levetiracetam in the sample, and even the concentration of the levetiracetam in the sample.

A certain embodiment provides a method of qualitatively determining the presence or absence of a levetiracetam in a sample, through the use of lateral flow chromatography. The basic design of the qualitative lateral flow device is as follows: 1) The sample pad is where the sample is applied. The sample pad is treated with chemicals such as buffers or salts, which, when redissolved, optimize the chemistry of the sample for reaction with the conjugate, test, and control reagents. 2) Conjugate release pad is typically a polyester or glass fiber material that is treated with a conjugate reagent such as an antibody colloidal gold conjugate. A typical process for treating a conjugate pad is to use impregnation followed by drying. In use, the liquid sample added to the test will redissolve the conjugate so that it will flow into the membrane. 3) The membrane substrate is usually made of nitrocellulose or a similar material whereby antibody capture components are immobilized. 4) A wicking pad is used in tests where blood plasma must be separated from whole blood. An impregnation process is usually used to treat this pad with reagents intended to condition the sample and promote cell separation. 5) The absorbent pad acts as a reservoir for collecting fluids that have flowed through the device. 6) The above layers and membrane system are laminated onto a plastic backing with adhesive material which serves as a structural member.

A certain embodiment provides a method of qualitatively determining the presence of a levetiracetam in a sample, through the use of lateral flow chromatography. In this embodiment, the membrane strip comprises a sample pad, which is a conjugate release pad (CRP) which comprises an antibody that is specific for the levetiracetam. This antibody is conjugated to a non-isotopic signal-generating moiety, such as a colloidal gold particle. Other detection moieties useful in a lateral flow chromatography environment include dyes, colored latex particles, fluorescently labeled latex particles, non-isotopic signal generating moieties, etc. The membrane strip further comprises a capture line, in which the levetiracetam derivative antigen is immobilized on the strip. In some embodiments, this immobilization is through covalent attachment to the membrane strip, optionally through a linker. In other embodiments, the immobilization is through non-covalent attachment to the membrane strip. In still other embodiments, the immobile levetiracetam derivative in the capture line is attached to a reactive partner, such as an immunogenic carrier like BSA.

Sample from a patient is applied to the sample pad, where it can combine with the antibody in the CRP, thus forming a solution. This solution is then allowed to migrate chromatographically by capillary action across the membrane. When the levetiracetam is present in the sample, a levetiracetam-antibody complex is formed, which migrates across the membrane by capillary action. When the solution reaches the capture line, the levetiracetam-antibody complex will compete with the immobile levetiracetam for the limited binding sites of the antibody. When a sufficient concentration of levetiracetam is present in the sample, it will fill the limited antibody binding sites. This will prevent the formation of a colored antibody-immobile levetiracetam complex in the capture line. Therefore, absence of color in the capture line indicates the presence of levetiracetam in the sample.

In the absence of levetiracetam in the sample, a colored antibody-immobile levetiracetam complex will form once the solution reaches the capture line of the membrane strip. The formation of this complex in the capture line is evidence of the absence of levetiracetam therapeutic in the sample.

A certain embodiment provides a method of quantitatively determining the amount of a levetiracetam in a sample, through the use of lateral flow chromatography. This technology is further described in U.S. Pat. Nos. 4,391,904; 4,435,504; 4,959,324; 5,264,180; 5,340,539; and 5,416,000, among others, which are herein incorporated by reference. In one embodiment, the antibody is immobilized along the entire length of the membrane strip. In general, if the membrane strip is made from paper, the antibody is covalently bound to the membrane strip. If the membrane strip is made from nitrocellulose, then the antibody can be non-covalently attached to the membrane strip through, for example, hydrophobic and electrostatic interactions. The membrane strip comprises a CRP which comprises the levetiracetam attached to a detector moiety. In a certain embodiment, the detector moiety is an enzyme, such as horseradish peroxidase (HRP).

Sample from a patient is applied to the membrane strip, where it can combine with the levetiracetam/detector molecule in the CRP, thus forming a solution. This solution is then allowed to migrate chromatographically by capillary action across the membrane. When the levetiracetam is present in the sample, both the sample levetiracetam and the levetiracetam/detector molecule compete for the limited binding sites of the antibody. When a sufficient concentration of levetiracetam is present in the sample, it will fill the limited antibody binding sites. This will force the levetiracetam/detector molecule to continue to migrate in the membrane strip. The shorter the distance of migration of the levetiracetam/detector molecule in the membrane strip, the lower the concentration of levetiracetam in the sample, and vice versa. When the levetiracetam/detector molecule comprises an enzyme, the length of migration of the levetiracetam/detector molecule can be detected by applying an enzyme substrate to the membrane strip. Detection of the product of the enzyme reaction is then utilized to determine the concentration of the levetiracetam in the sample. In a certain embodiment, the enzyme's color producing substrate such as a modified N,N-dimethylaniline is immobilized to the membrane strip and 3-methyl-2-benzothiazolinone hydrazone is passively applied to the membrane, thus alleviating the need for a separate reagent to visualize the color producing reaction.

Fluorescence Polarization Immunoassay for Levetiracetam

Fluorescence polarization immunoassay (FPIA) technology is based upon competitive binding between an antigen/drug in a sample and a known concentration of labeled antigen/drug. FPIA technology is described in, for example, U.S. Pat. Nos. 4,593,089, 4,492,762, 4,668,640, and 4,751,190, which are incorporated herein by reference. Accordingly, the FPIA reagents, systems, and equipment described in the incorporated references can be used with anti-levetiracetam antibodies which are also anti-levetiracetam analog antibodies.

The FPIA technology can be used to identify the presence of levetiracetam and can be used in assays that quantify the amount of levetiracetam in a sample. In part, the rotational properties of molecules in solution allow for the degree of polarization to be directly proportional to the size of the molecule. Accordingly, polarization increases as molecular size increases. That is, when linearly polarized light is used to excite a fluorescent-labeled or other luminescent-labeled levetiracetam or derivative thereof, which is small and rotates rapidly in solution, the emitted light is significantly depolarized. When the fluorescent-labeled levetiracetam or derivative interacts with or is bound to an antibody, the rotation is slowed and the emitted light is highly polarized. This is because the antibody significantly and measurably increases the size of the complex. Also, increasing the amount of unlabeled levetiracetam in the sample can result in decreased binding of the fluorescent-labeled levetiracetam or derivative by the anti-levetiracetam antibody, and thereby decrease the polarization of light emitted from sample. The quantitative relationship between polarization and concentration of the unlabeled levetiracetam in the sample can be established by measuring the polarization values of calibrations with known concentrations of levetiracetam. Thus, FPIA can be used to identify the presence and concentration of levetiracetam in a sample.

In one embodiment, the assay involves an FPIA assay system. An example of components of the FPIA system can include the following: i) monoclonal or polyclonal anti-levetiracetam antibodies capable of specifically binding to levetiracetam and a levetiracetam derivative; ii) a sample suspected of containing the levetiracetam; and iii) levetiracetam derivative labeled with a fluorescent moiety, such as fluorescein. Alternatively, the system can be provided as a kit exclusive of the sample. Additionally, the system can include various buffer compositions, levetiracetam concentration gradient compositions or a stock composition of levetiracetam, and the like.

Homogeneous Microparticle Immunoassay for Levetiracetam

Homogeneous microparticles immunoassay ("HMI") technology, which can be referred to as immunoturbidimetric assays, is based on the agglutination of particles and compounds in solution. When particles and/or chemical compounds agglutinate, particle sizes can increase and increase the turbidity of a solution. Accordingly, anti-levetiracetam antibodies can be used with microparticles and levetiracetam derivatives in order to assess the presence, and optionally the amount, of levetiracetam in a sample. HMI technologies can be advantageous because the immunoassays can be performed on blood, blood hemolysate, serum, plasma, tissue, and/or other samples. HMI assays can be configured to be performed with levetiracetam and/or a levetiracetam derivative loaded onto a microparticle, or with an anti-levetiracetam antibody loaded onto a microparticle. HMI or immunoturbidimetric assays are well known in the art for measuring agglutination of substances in a sample.

Immunoturbidimetric assay technologies are described in, e.g., U.S. Pat. Nos. 5,571,728, 4,847,209, 6,514,770, and 6,248,597, which are included herein by reference. Such assays involve light attenuation, nephelometric, or turbidimetric methods. The formation of an agglutinated compound AB from levetiracetam (A) and anti-levetiracetam antibody microparticle binding partner (B) can be measured by the change which occurs in the scattering or absorption of the incident light directed into the sample. Alternatively, the anti-levetiracetam antibody (A) can bind with a levetiracetam or derivative loaded microparticle. When suspendable particles having an immobilized binding partner are used, there is an enhancement of the effects, which makes it possible to determine considerably lower levetiracetam concentrations. These homogeneous methods can be carried out quickly and simply, and permit, in particular, the automation of sample analyses as described in more detail below.

Cloned Enzyme Donor Immunoassays for Levetiracetam

Cloned enzyme donor Immunoassays ("CEDIA®", Roche Diagnostics), as are based upon the competition of levetiracetam in the biological sample with a levetiracetam conjugate containing an inactive genetically engineered enzyme-donor ("ED") fragment such as from β-D-galactoside galactohydrolase or β-galactosidase ("β-gal") from E. coli, for binding to an antibody capable of binding levetiracetam. If levetiracetam is present in the sample it binds to the antibody, leaving the ED portion of the ED-derivative conjugate free to restore enzyme activity of β-D-galactoside galactohydrolase or B gal in the reaction mixture so as to be capable of association with enzyme acceptor ("EA") fragments. The active enzyme comprised of the ED and EA is then capable of producing a quantifiable reaction product when exposed to an appropriate substrate. A preferred substrate is chlorophenol red-β-D-galactopyranoside ("CPRG"), which can be cleaved by the active enzyme into galactose and CPR, wherein CPR is measured by absorbency at about wavelength 570 nm. In the instance levetiracetam is not present in the sample, the antibody binds to the ED-derivative conjugate, thereby inhibiting association of the ED fragments with the EA fragments and inhibiting restoration of enzyme activity. The amount of reaction product and resultant absorbance change are proportional to the amount of levetiracetam in the sample.

Chemiluminescent Heterogeneous Immunoassays for Levetiracetam

A competitive assay using chemiluminescent microparticle immunoassay ("CMIA") technology can also be used to assess whether or not levetiracetam is present in a sample. Various types of CMIA technologies are well known in the art of heterogeneous immunoassays for determining the presence and/or amount of a chemical entity in a sample. CMIA assays can include the use of anti-levetiracetam antibodies, which are capable of binding to levetiracetam and its derivatives, which are coupled to particles, such as magnetic particles or particles suitable for separation by filtration, sedimentation, and/or other means. Additionally, a tracer, which can include a levetiracetam derivative linked to a suitable chemiluminescent moiety, can be used to compete with free levetiracetam in the patient's sample for the limited amount of anti-levetiracetam antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free drug in the patient's sample and concentration is determined by constructing a standard curve using known values of the drug.

Other Immunoassays for Levetiracetam

The levetiracetam derivatives, conjugates, antibodies, immunogens, and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the levetiracetam derivatives, conjugates, antibodies, immunogens and/or tracers, such assays can also be modified as is well known in the art. As such, various modifications of steps or acts for performing such immunoassays can be made within the scope of the embodiments.

Kits

The present disclosure also provides kits that find use in practicing the subject methods, as described above. The kits of the embodiments can comprise an anti-levetiracetam antibody in a container, and may comprise a levetiracetam conjugate (e.g., for use in a competitive binding assay, for use in an enzyme-based assay, and the like). The kits may also include a calibration standard and/or control standard useful in performing the assay; and, optionally, instructions on the use of the kit. Kit components can be in a liquid reagent form, a lyophilized form, or attached to a solid support. The reagents may each be in separate containers, or various reagents can be combined in one or more containers depending on cross-reactivity and stability of the reagents. The sample, suspected of containing a levetiracetam, and a calibration material, containing a known concentration of the levetiracetam, are assayed under similar conditions. Levetiracetam concentration is then calculated by comparing the results obtained for the unknown specimen with results obtained for the standard. This is commonly done by constructing a calibration or dose response curve.

Various ancillary materials may be employed in an assay in accordance with the embodiments. In a certain embodiment, buffers and/or stabilizers are present in the kit components. In a certain embodiment, the kits comprise indicator solutions or indicator "dipsticks", blotters, culture media, cuvettes, and the like. In a certain embodiment, the kits comprise indicator cartridges (where a kit component is bound to a solid support) for use in an automated detector. In a certain embodiment, additional proteins, such as albumin, or surfactants, particularly non-ionic surfactants, may be included. In a certain embodiment, the kits comprise an instruction manual that teaches a method of the embodiments and/or describes the use of the components of the kit. Reagents and buffers used in the assays can be packaged separately or in combination into kit form to facilitate distribution. The reagents are provided in suitable containers, and typically provided in a package along with written instructions relating to assay procedures.

An embodiment of the present disclosure relates to a kit for conveniently determining the presence or the absence of levetiracetam in a sample. The kit may comprise an anti-levetiracetam antibody and a levetiracetam calibration standard. The levetiracetam calibration standard may comprise calibration and control standards useful in performing the assay. The kits can also optionally comprise a conjugate comprising a levetiracetam moiety and a detectable signal. In a certain embodiment, a detectable signal of the conjugate is an enzyme. In yet another embodiment, the enzyme is glucose-6-phosphate dehydrogenase (G6PDH). In one embodiment, the G6PDH is a variant of a naturally-occurring G6PDH in which one or more lysine residues are deleted or substituted, or one or more cysteine residues are introduced.

EXAMPLES

The following examples are offered by way of illustration and not by way of limitation. It should be apparent that the invention can include additional embodiments not illustrated by example. Additionally, many of the examples have been performed with experimental protocols well known in the art using the levetiracetam derivatives, antigens, immunogens, and anti-levetiracetam derivative antibodies prepared in accordance with the present invention.

Example 1

Scheme 1 is a Schematic Representation of a Chemical Reaction Showing the Reaction Between (S)-2-aminobutyramide (3) and Methyl Itaconate (4) for Synthesizing (2S)-2-[4-(aminomethyl)-2-oxo-1-pyrrolidinyl]-butanamide HCl Derivative (11) of Levetiracetam Based on Benoit et al., J. Med. Chem. 2004, 47, 530-549

Transformation of the ester function of (5), into the mesylate (9) using standard conditions allows the introduction of azide functionality. Hydrogenolysis of the azide (10) affords the aminomethyl derivative (11). Oxidation of (6) with $KMnO_2$ affords compound (7). Treating compound (5) with NaOH and MeOH then HCl affords compound (8).

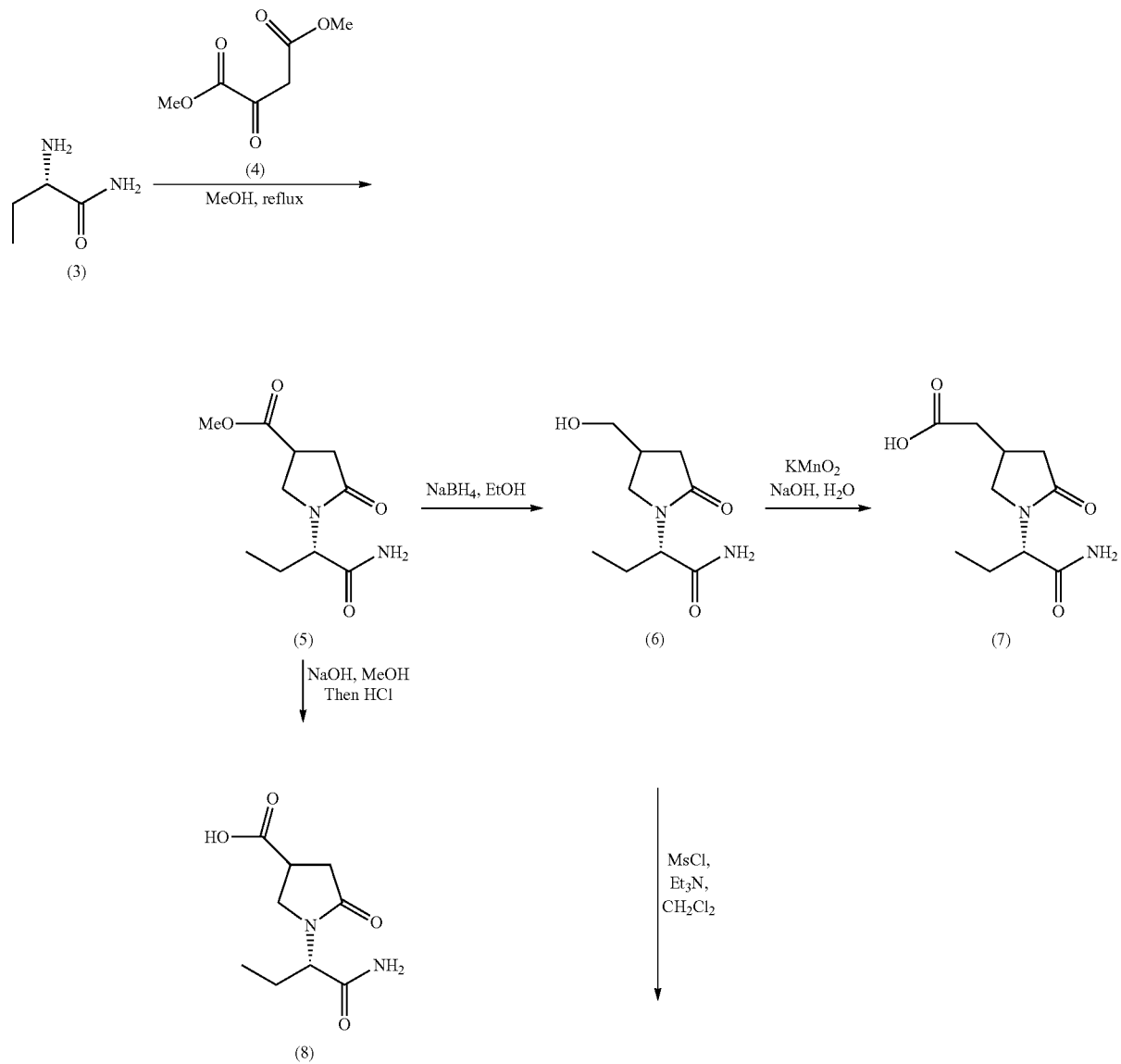

SCHEME 1

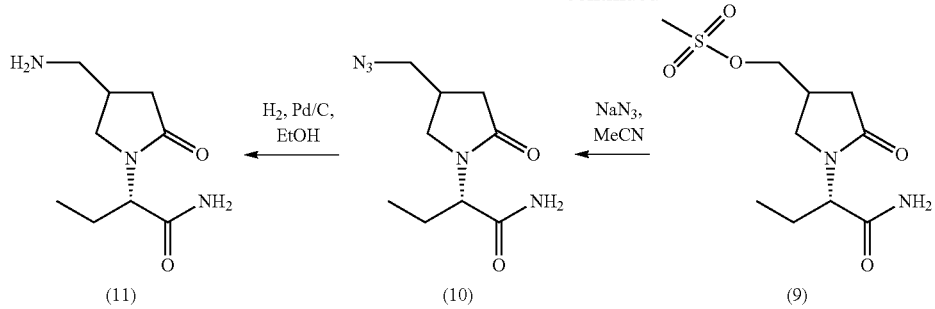

Example 2

Scheme 2 is a Schematic Representation of a Chemical Reaction Showing the Reaction Between (S)-2-aminobutyramide (3) and Compound (12) Giving 1-((1S)-1-Carbamoylpropyl)-2-oxopyrrolidine-3-carboxylic Acid (13) and (2S)-2-(3-Hydroxymethyl-2-oxopyrrolidin-1-yl)butyramide (14) Followed by Oxidation to Give (15) Based on (Benoit et al., J. Med. Chem. 2004, 47, 530-549)

Using mechanical stirring, under inert atmosphere, a solution of 6,6-dimethyl-5,7-dioxaspiro[2.5]octane-4,8-dione (12) and (2S)-2-aminobutanamide (3) in MeCN is warmed to 65° C. for 2 h. Another portion of (12) is added. After 3.5 h at 60° C., the reaction mixture is left overnight at room temperature. The precipitate is filtered, is dissolved in water, and is purified on ion-exchange resin (AG50W-X4) with water, and the acidic fractions (pH <2) are collected to afford (13).

Using mechanical stirring, under inert atmosphere, CH$_3$I is added dropwise to a suspension of K$_2$CO$_3$ and (13) in acetone at room temperature. The mixture is refluxed, and a second portion of CH$_3$I is added dropwise. The reaction mixture is left overnight at room temperature, is refluxed, is cooled to room temperature, and is concentrated in vacuo. The filtrate is extracted with AcOEt and is evaporated to dryness to afford a crude methyl ester which is used without further purification. Using a magnetic stirrer, under inert atmosphere, NaBH$_4$ is added to a mixture of the crude methyl ester in t-BuOH at room temperature. After heating at 80° C., the reaction mixture is cooled to room temperature and is quenched with water (1 l), and t-BuOH is removed in vacuo (bath temperature 30° C.). The aqueous layer is saturated with NaCl, is lowered to pH 6.8, is extracted with CHCl$_3$-MeOH (80/20 (v/v)), and is concentrated to dryness to afford a crude alcohol (14). Treating compound (14) with KMnO$_2$, NaOH and H$_2$O can then afford compound (15).

SCHEME 2

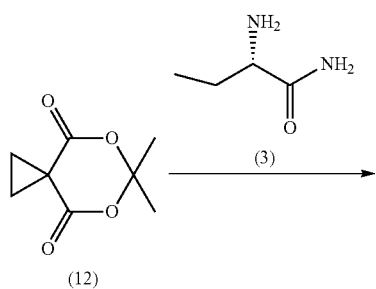

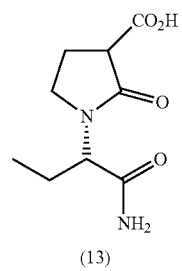

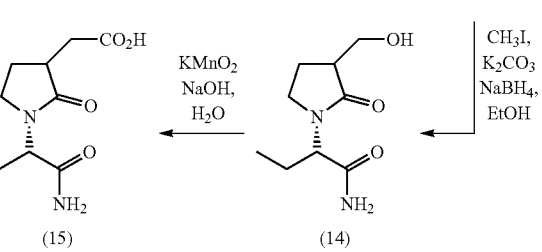

Example 3

Scheme 3 is a Schematic Representation of a Chemical Reaction Depicting the Acylation Reaction of Aminomethyl Derivative of Levetiracetam (11) with Succinic Anhydride to Give Compound (16)

A solution of (11) in tetrahydrofuran (anhydrous) is combined with N,N-diisopropylethylamine (DIPEA), and is stirred under argon. Succinic anhydride and 4-dimethylaminopyridine (DMAP) are added to the above solution to form a reaction mixture. The reaction mixture is stirred under argon for 12 hours, and the solvent is evaporated under reduced pressure to form a residue. The residue is purified by flash column chromatography with ethyl acetate as an eluent. The fractions containing the succinyl derivative (16) are combined and are concentrated to yield a final product.

SCHEME 3

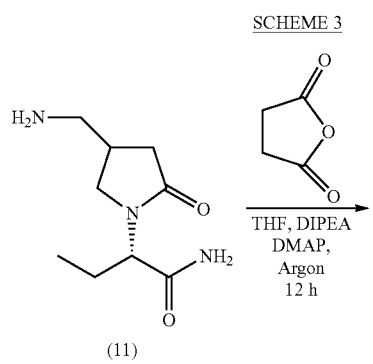

Example 4

Scheme 4 is a Schematic Representation Depicting the Thiolating Reaction for Introducing Sulphur into the Aminomethyl Derivative of Levetiracetam (11) Yielding Compound (18)

To a stirred solution of (11) in THF is added diisopropylethylamine N-succinimidyl-S-acetylthioacetate. The reaction mixture is stirred at room temperature. TLC analysis of the mixture would show a new spot as a product in comparison with (11). The organic solvent is removed to dryness by rotary evaporation under reduced pressure. The residue is purified by flash column chromatography (silica gel) using ethyl acetate/hexane (7/3) as an eluent to afford compound (17).

To a solution of (17) in degassed ($N_2$) MeOH and $H_2O$ is added $K_2CO_3$ under nitrogen. The reaction mixture is stirred at room temperature under nitrogen for 1 hour. TLC analysis of the mixture would show that starting material (17) disappears and a new spot is formed as a product (silica gel, MeOH/$CH_2Cl_2$=1/9, $I_2$, Ellman's reagent). MeOH is filtered to remove excess $K_2CO_3$ and the filtrate is concentrated by rotary evaporation in room temperature. The residue is dried under high vacuum for 0.5 hour at room temperature to afford compound (18).

SCHEME 4

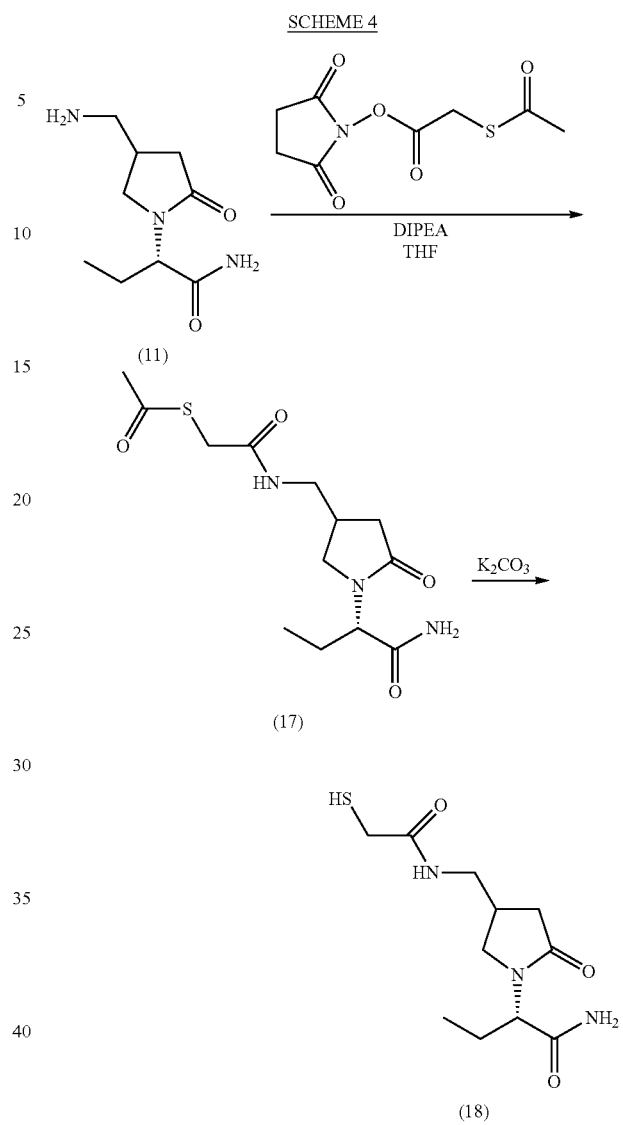

Example 5

Scheme 5 is a Schematic Representation of a Acylation of Levetiracetam Derivative (11) with Bromoacetic N-Hydroxyl Succinimide Under Basic Condition to Give Compound (19)

To a solution of compound (11) in tetrahydrofuran (anhydrous) are added N,N-diisopropylethylamine and a solution of bromoacetic N-hydroxyl succinimide in tetrahydrofuran at 0° C. under argon. The reaction is stirred at room temperature. Water is added and most of tetrahydrofuran is removed by rotary evaporation. The aqueous phase is extracted with $CH_2Cl_2$. The combined organic phase is washed with water and is dried over MgSO4. The organic phase is filtered and is concentrated to dryness. The residue is purified by flash column chromatography (silica gel) using ethyl acetate/hexane (2/3) as an eluent to afford compound (19).

SCHEME 5

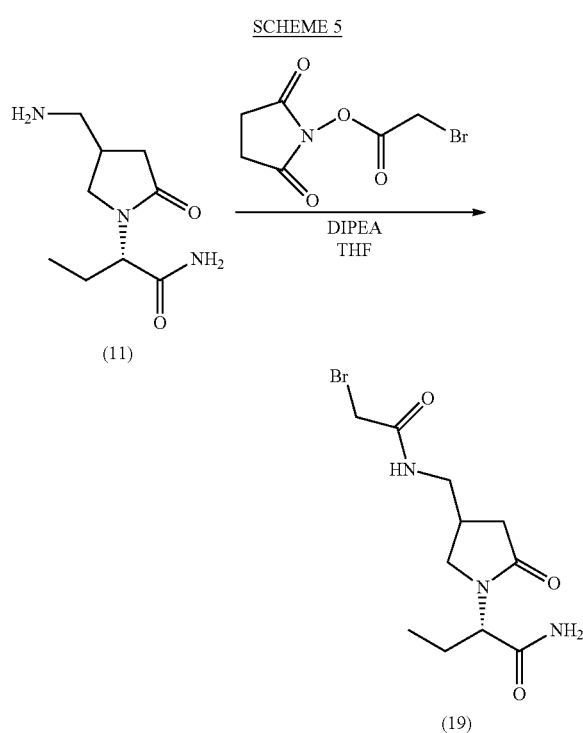

Example 6

Scheme 6 is a Schematic Representation for the Synthesis of Compound (25)

Rink amide resin (0.51 mequiv/g, 100-200 mesh) is placed in a glass vessel and is stirred in 20% v/v piperidine/DMF for 0.5 h. The resin is drained and the entire deprotection is repeated. The resin is filtered, is washed (6×DMF), and is dried. The resin is suspended in DMF and is treated with 9-fluorenylmethoxycarbonyl-N-ε-tert-butyloxycarbonyl-L-ornithine (19) followed by a solution of 1,3-diisopropyl carbodiimide and HOBt in DMF. The reaction mixture is stirred for 1 h at room temperature and then is filtered and is washed (DMF), and the coupling process is repeated. The resin is filtered, is washed (6×DMF, 6×CH$_2$Cl$_2$), is dried, and is used as it stands in the next steps (20). Amide resin is contained within a fitted polypropylene syringe. Removal of the Fmoc group is achieved using 20% piperidine in DMF to give compound (21). To the amino resin is added 4-oxobutyric acid 4-methoxybenzyl ester in (MeO)$_3$CH. The resin is stirred and then is filtered, is washed with CH$_2$Cl$_2$, and is treated with sodium triacetoxyborohydride. The reaction mixture is stirred for 18 h at room temperature and then is filtered; is washed in the solvent sequence MeOH, 3×CH$_2$Cl$_2$, 3×MeOH; and is dried (22). The N-Alloc protected amine is deprotected with Pd(PPh$_3$)$_4$, borohydride in DCM:MeOH:H$_2$O (5:4:1, v/v) is stirred at room temperature for 1 hour (23). To a suspension of resin (23) in tetrahydrofuran (anhydrous) is added N,N-diisopropylethylamine and a solution of bromoacetic N-hydroxyl succinimide in tetrahydrofuran at 0° C. under argon. The reaction mixture is stirred at room temperature for 2 hours. Water is added and most of tetrahydrofuran is removed by rotary evaporation. The aqueous phase is extracted with CH$_2$Cl$_2$ (3×30 mL). The combined organic phase is washed with water and is dried over MgSO$_4$. The organic phase is filtered and is concentrated to dryness. The residue is purified by flash column chromatography (silica gel) using ethyl acetate/hexane (2/3) as an eluent to afford compound (24).

The resin is suspended in trifluoroacetic acid/H$_2$O (95/5) with 5% of triisopropylsilane with vortex agitation and then is filtered and is washed (CH$_2$Cl$_2$×2). The filtrate is concentrated and the residue is dissolved in CH$_2$Cl$_2$ and is concentrated once more. The desired compound (25) is purified.

SCHEME 6

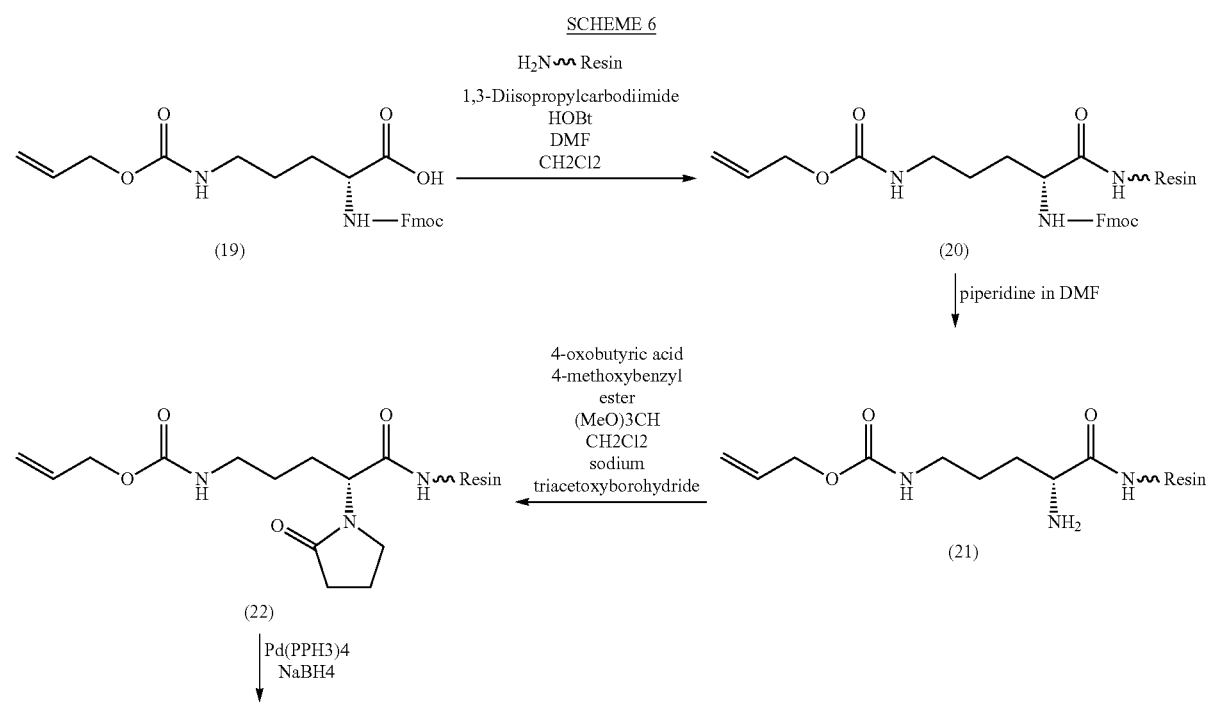

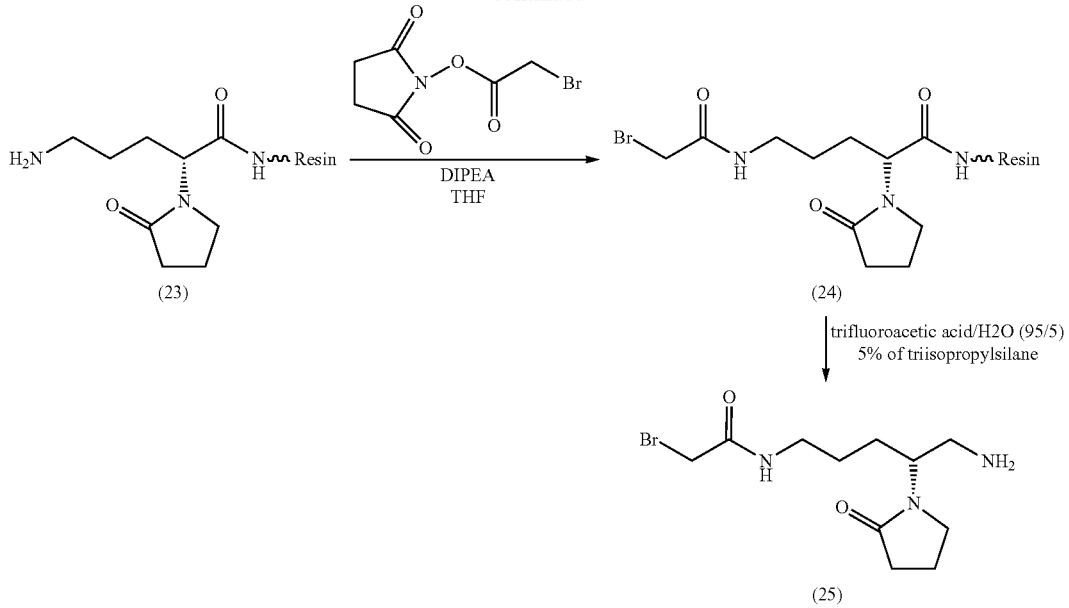
Example 7
Scheme 7 is a Schematic Representation of Synthesis of Levetiracetam Derivative (30)   30
Compound (30) can be synthesized similarly as described in Example 6 using N-α-Fmoc-L-glutamic acid γ-t-butyl ester (26) as the starting material.
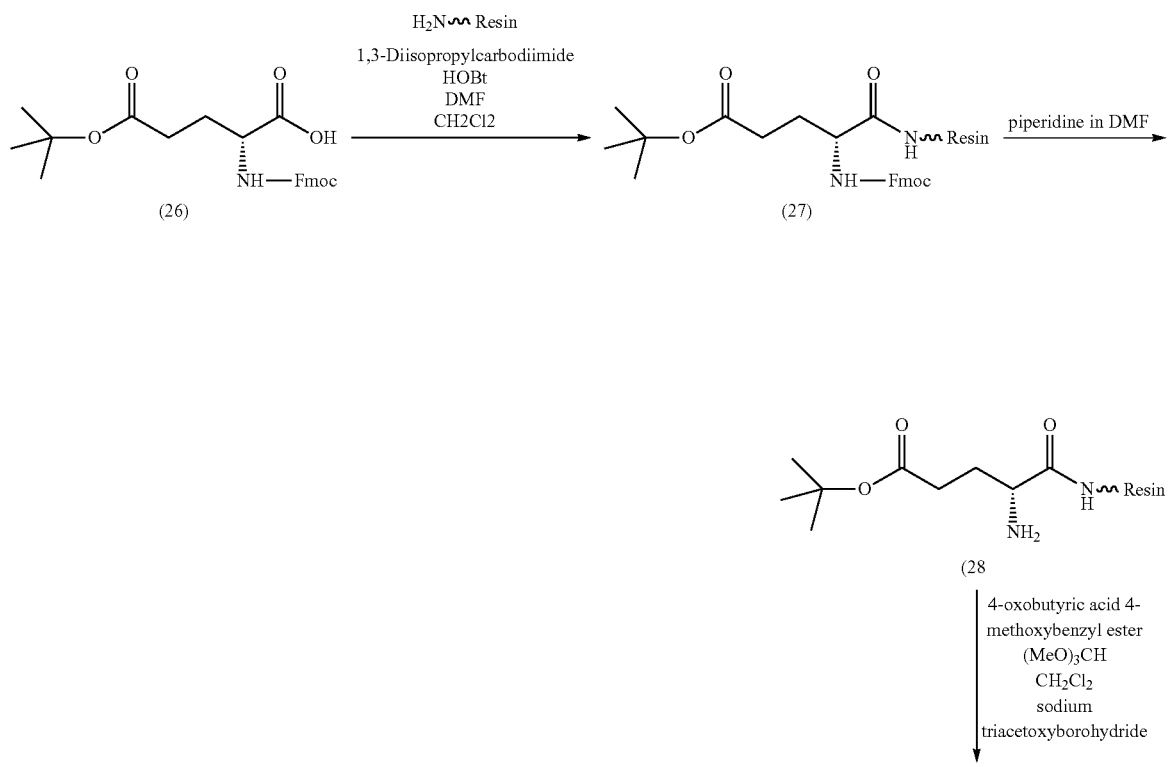

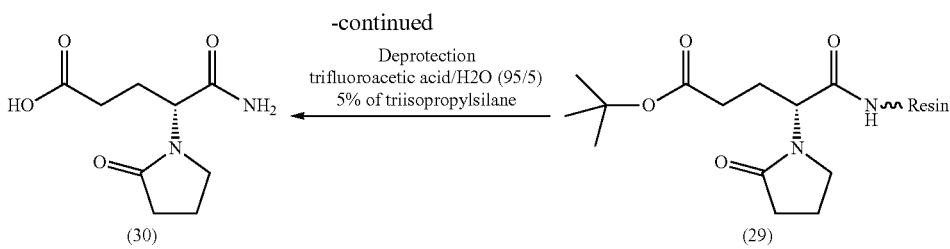

Example 8

Scheme 8 is a Schematic Representation of Synthesis of Levetiracetam Derivative (30)

Compound (31) can be synthesized similarly as described in Example 6 using Fmoc-S-trityl-L-homocysteine (32) as the starting material.

SCHEME 8

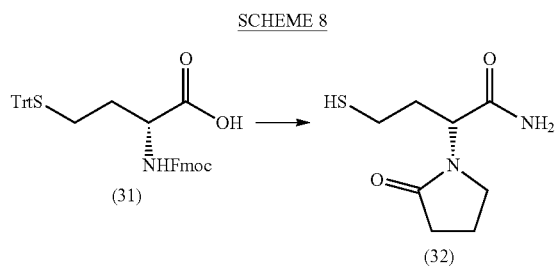

Example 9

Scheme 9 is a Schematic Representation of a Chemical Reaction for Converting a Levetiracetam Derivative (11) into an Immunogen (11-KLH)

Lyophilized succinylated KLH (33) (Sigma) is reconstituted with deionized water. The KLH solution is dialyzed overnight with two changes MES buffer (0.1 M MES, 0.9 M NaCl, 0.02% NaN3, pH 4.7). After dialysis, succinylated KLH is transferred to a reaction vial. Compound (11) is dissolved in dry DMF and is added to the reaction vial slowly. EDC (Pierce) is dissolved in deionized water and is immediately added to KLH solution. Additional EDC aliquots (10 per addition) are added until slight precipitation occurred during the conjugation reaction. The reaction is allowed to proceed for approximately 2 h under constant mixing at room temperature to give immunogen (11-KLH). The reaction mixture is then dialyzed against three changes of HEPES buffer (0.05 M, pH 7.2, 1 mM EDTA).

SCHEME 9

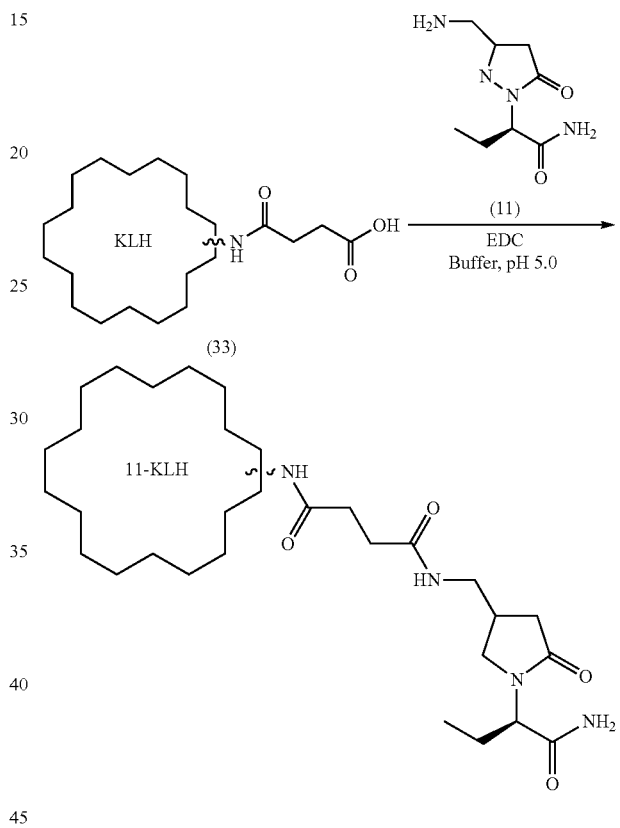

Example 10

Schemes 10A-10F are Schematic Representations for the Synthesis of Compound (44)

In a 10-L, three-necked flask fitted with mechanical stirrer and refluxing condenser, under nitrogen atmosphere, 1,226 g (12 mol, 1 equiv) of (2S)-2-aminobutanamide and 1,912 mL (2,150 g, 13.2 mol, 1.1 equiv) of dimethyl itaconate is dissolved in 6.13 L of MeOH. The mixture is refluxed for 10 h and cooled slowly to 20° C. over 4 h. It was filtered, the precipitate is washed with MeOH, and the combined organic phases are concentrated to dryness to give 3283 g of the crude intermediate. In a 20-L, three-necked flask fitted with a mechanical stirrer, Rashig column, and distillation arm, under inert atmosphere, the above obtained, crude intermediate and 84.7 g (891 mmol, 0.1 equiv) of 2-hydroxypyridine is dissolved in 11.6 L of toluene. The mixture is refluxed and the methanol formed is distilled off for 8 h until 480 mL of methanol is collected. The mixture is cooled and concentrated to dryness to give 2,187 g of crude amide ester as a mixture of diastereoisomers in a 57.5/42.5 ratio.

The two diastereoisomers is separated by preparative LC Chiral Phase (Chiralpak AD 100 500 mm, EtOH H₂O 99.9/0.1)-column, the eluate is concentrated to dryness to give 968 g of the crude 1 (first eluted compound). The crude (34) is recrystallized from 2 L of AcOEt to give 676 g of pure compound (34).

SCHEME 10A

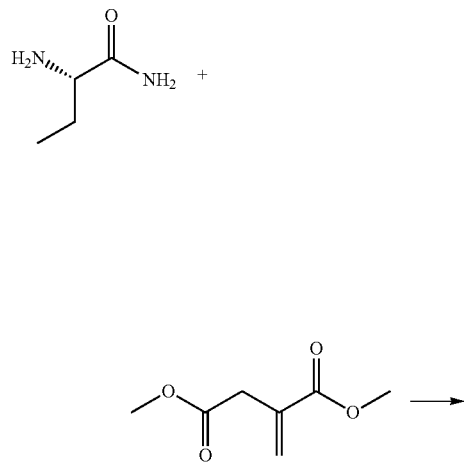

SCHEME 10B

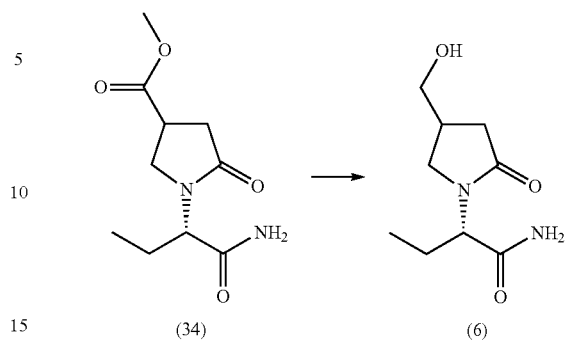

In a 4 L, three necked flask fitted with mechanical stirrer, dropping funnel and refluxing condenser under inert atmosphere, 114 g (56 mmol, 1 equiv) of compound (6) is dissolved in 2 L of CH₂Cl₂ and cooled to 0° C. Dry triethylamine (158.5 mL, 115 g, 2 equiv) is added in one portion, followed by dropwise addition of a solution o 66.3 mL (96.2 g, 1.5 equiv) of methanesulfonyl chloride in 19 mL of CH₂Cl₂ over 1 h, while the temperature is maintained below 4° C. After 4 h, 7.5 mL of methanesulfonyl chloride and 15 mL of triethylamine are added, and the mixture is kept overnight in the refrigerator. The mixture is filtered, the residue is washed with CH₂Cl₂, and the combined organic phases are concentrated to dryness to give 216 g crude compound (9).

SCHEME 10C

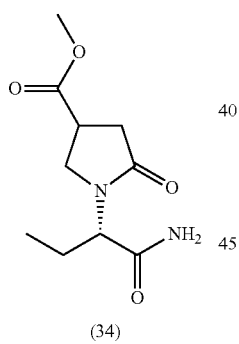

In a 2-L three-necked flask fitted with mechanical stirrer and reflux condenser, under inert atmosphere, a solution of 133 g (583 mmol, 1 equiv) of compound (34) in 200 mL of EtOH is added to 300 mL of EtOH, and the mixture is cooled to 0° C. Solid NaBH4 (66.2 g, 1.74 mol, 12 equiv) is then added by portions over 1.5 h, while the temperature is maintained between 2 and 4° C. After 2 h, the temperature is raised to 12° C. for 1 h and lowered again to 2-4° C. Then, 240 mL of a saturated solution of NH₄Cl is added dropwise over 1 h, followed by 120 mL of acetone, and the mixture is left overnight at room temperature. The mixture is filtered and the precipitate washed with 370 mL of EtOH. The combined organic fractions are concentrated to dryness to give 148 g of crude product. It is suspended in 300 mL of CH₂Cl₂, stirred for 0.5 h, filtered, washed with 2100 mL of CH₂Cl, and dried to give 114 g of compound (6).

To a stirred solution of compound (9) (1.128 mg, 5 mmol) was added sodium cyanide (0.6 g, 10 mmol) in DMSO (20 ml). The mixture solution was stirred at room temperature for 1 h and then to 100° C. for 3 h. The organic phase was filtered and the filtrate was concentrated under reduced pressure gave crude (35) as a white solid (0.3 g, 50% yield).

SCHEME 10D

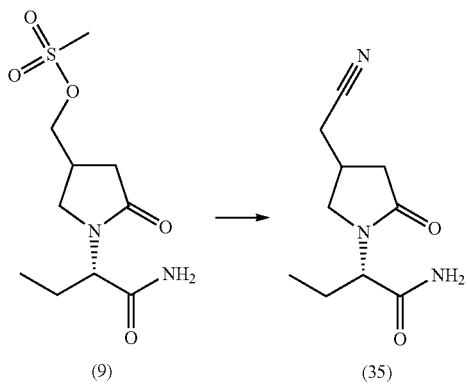

To a solution of (35) (8.29 g; 21.20 mmol) and cobaltous chloride hexahydrate (10.08 g 42.40 mmol) in 99% MeOH (350 mL) and THF (120 mL), was added NaBH$_4$ (8.04 g; 212 mmol) in portions. Evolution of hydrogen gas was observed as well as the formation of a black precipitate. When the addition was complete, stirring was continued for 2 h at room temperature. HCl (2 M, 70 mL) was then poured in the reaction mixture in order to dissolve the black precipitate. After removal of MeOH and THF, the aqueous layer was made alkaline by the addition of concentrated NH$_4$OH and then extracted with diethyl ether (4×200 mL). The combined extracts were washed with saturated sodium chloride solution, dried (MgSO$_4$), filtered and evaporated in vacuo. The crude product was chromatographed on a 4.5×30 cm column of silica gel gave pure (36) as a white solid (4.46 g).

SCHEME 10E

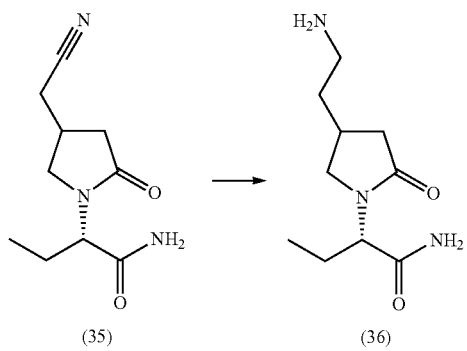

To a stirred solution of compound (36) (464 mg, 1 mmol) was added 2-bromoacetyl bromide (200 mg, 1 mmol) in DCM (30 ml). The mixture solution was stirred at room temperature for 1 h and then water was added to the solution. The organic phase was dried with Na$_2$SO$_4$. The organic phase was filtered and the filtrate was concentrated under reduced pressure gave crude (44) as a yellow solid (460 mg, 0.8 mmol, 80% yield).

SCHEME 10F

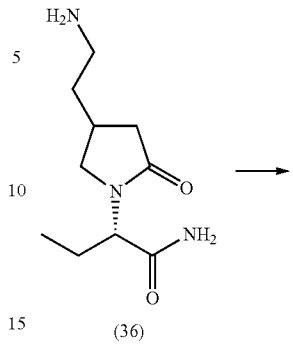

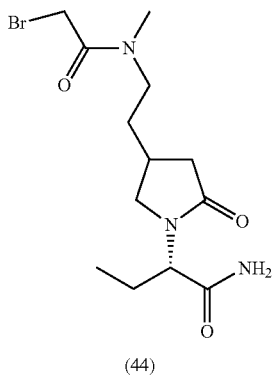

Example 11

Scheme 11 is a Schematic Representation of a Chemical Reaction for Converting a Levetiracetam Analog Ester (13) into KLH Immunogen (12-KLH)

To a stirred solution of (12) in dried DMF is added 1-ethyl-3-(3-dimethylamino propyl)carbodiimide (EDAC) and N-hydroxysuccinimide (NHS) at ice bath temperatures. The mixture is stirred overnight to form compound (13). Ester formation is monitored by TLC analysis.

Two vials of lyophilized KLH (Pierce) is reconstituted with deionized water each and are pooled. The mixture is allowed to stand overnight at 4° C. A buffer exchange is done by dialyzing overnight the KLH solution against sodium bicarbonate buffer (0.1 M, pH 8.9). An aliquot of the KLH preparation is transferred into a reaction vial. The solution of (13) is slowly added (10-20 µL per addition) to the solution of KLH (34) over a period of 2 h at ice bath temperatures. After the addition is completed, the mixture is stirred in a 4° C. cold room overnight. This solution is then dialyzed against three changes of HEPES buffer (10 mM, pH 7.0, 1 mM) gives immunogen (12-KLH).

Haptens (7), (8), (16), and (30) are conjugated with KLH using a conjugation procedure similar to that described above.

SCHEME 11

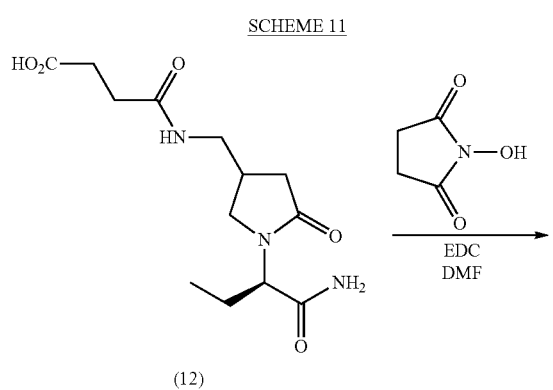

(12)

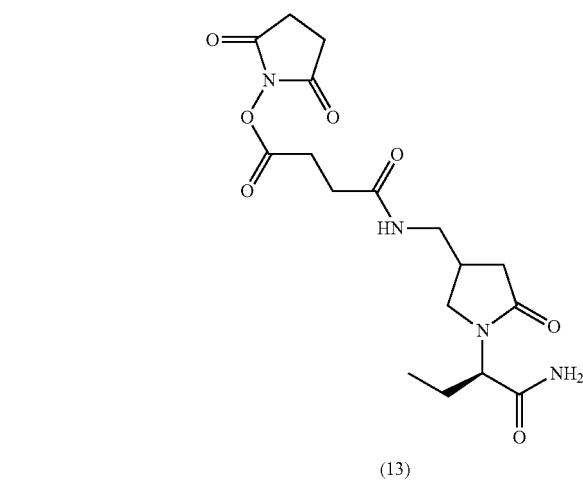

(13)

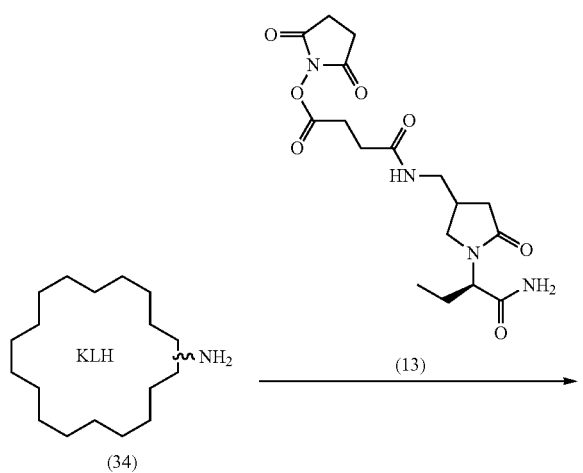

(34)

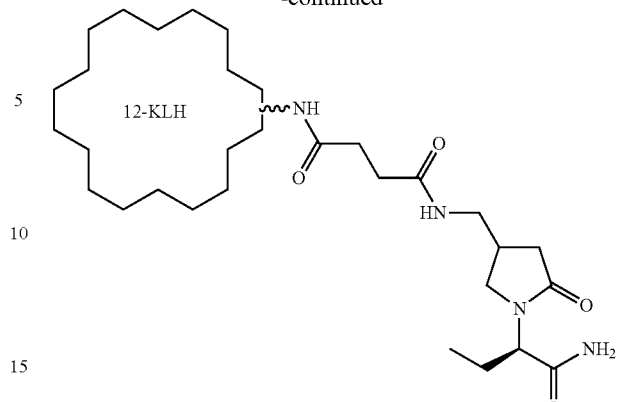

Example 12

Scheme 12 is a Schematic Representation of a Chemical Reaction for Converting a Levetiracetam Derivative Ester (13) into Glucose-6-Phosphate Dehydrogenase Conjugate (12-G6PDH)

Lyophilized G6PDH (Worthington Biochem. Corp.) is reconstituted with deionized water. The mixture is allowed to stand overnight at 4° C. The mixture is then dialyzed overnight at 4° C. against sodium bicarbonate buffer (0.1 M, pH 8.9). After dialysis, the enzyme solution is transferred to a reaction vial.

Activated product compound (13) is added in 5 to 10 µL quantities to a solution of glucose-6-phosphate dehydrogenase (G6PDH, 0.1 M in sodium carbonate buffer) glucose-6-phosphate (G6P, 4.5 mg/mg G6PDH), and NADH (9 mg/mg G6PDH) in a pH 8.9 sodium carbonate buffer at ice bath temperature. After the addition of each portion of solution of compound (13) a 2 µL aliquot is taken and is diluted 1:500 with enzyme buffer. A 3 µL aliquot of this diluted conjugation mixture is assayed for enzymatic activity similar to that described in Example 17 below. The reaction is monitored and is stopped at approximately 65% deactivation of enzyme activity. The mixture is desalted with a PD-10 pre-packed Sephadex G-25 (Pharmacia, Inc.) and pre-equilibrated with HEPES buffer (10 mM, pH 7.0, 1 mM EDTA). The reaction mixture is applied to the column and the protein fractions pooled. The pooled fractions are dialyzed against three (1.0 L each) changes of HEPES (10 mM, pH 7.0, 1 mM EDTA) to yield a solution of conjugate (12-G6PDH).

Haptens (7), (8), (16), and (30) are conjugated with G6PDH using a conjugation procedure similar to that described above.

SCHEME 12

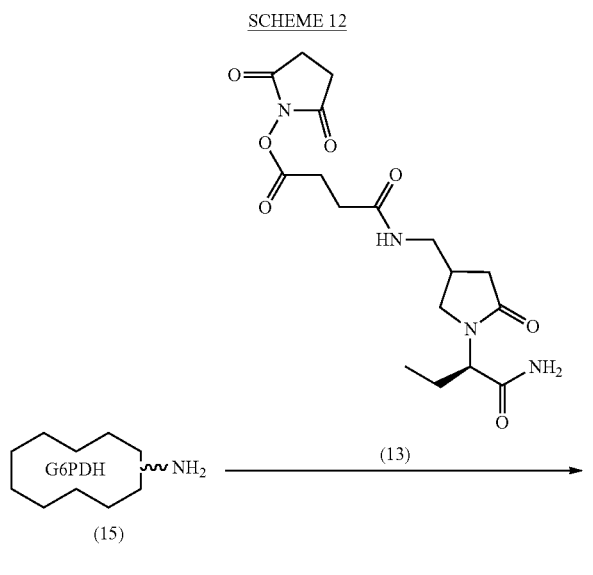

Example 13

Scheme 13 is a Schematic Representation of a Chemical Reaction for Converting KLH (34) into Bromoacetyl-KLH (36)

To a solution of KLH (20 mg) in $NaH_2PO_4$—$Na_2HPO_4$ buffer (pH=8.0, 0.1M, 2.0 mL) at 4° C. (ice-bath) was added a solution of bromoacetic acid NHS ester (5.8 mg, 0.024 mmol) in DMF (0.2 mL). The pH value was maintained at 8.0. The reaction mixture was stirred in the cold-room (4° C.) for 16 hours. The mixture was purified by a Sephadex G-50 column, eluting with $NaH_2PO_4$—$Na_2HPO_4$ buffer (pH=7.00, 0.025 M). The eluted fractions from the column were monitored by UV at 280 nm. A clean separation between bromoacetyl-KLH and the hapten was obtained. Fractions containing the product are pooled together (8.0 mL) and concentrated to 3.0 mL of bromoacetyl-KLH (36) by an Amicon concentrator for the next reaction.

SCHEME 13

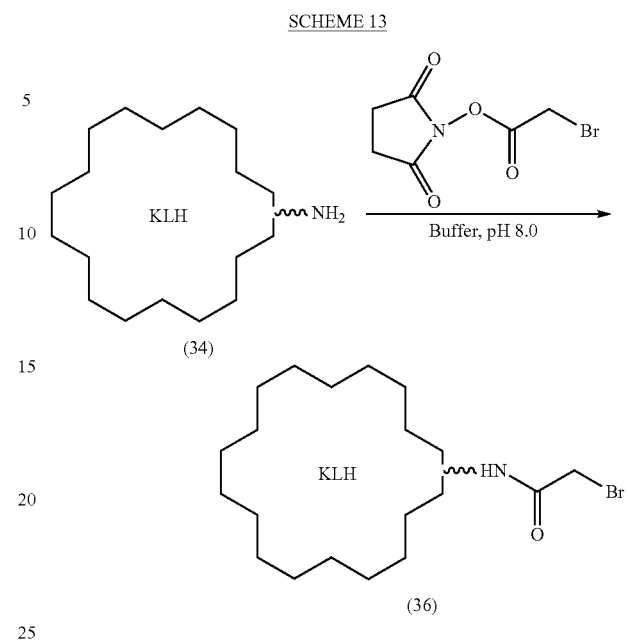

Example 14

Scheme 14 is a Schematic Representation of a Chemical Reaction for Converting a Levetiracetam (18) Analog into a KLH Immunogen (18-KLH)

To a solution of bromoacetyl-KLH (36) (pH=8.00) is added the levetiracetam derivative (18) solution slowly at 4° C. under nitrogen. The pH value is maintained at 8.0. The reaction is stirred at 4° C. (cold room) for 16 hours. The reaction mixture is separated using a Sephadex G-25 column equilibrated with $NaH_2PO_4$—$Na_2HPO_4$ buffer (pH=7.0, 0.1 M). The UV detector at 280 nm can be used to monitor the eluted fractions from the column. A clean separation between KLH immunogen and the hapten can be obtained. Fractions containing protein are pooled and are concentrated. The concentration of immunogen (18-KLH) is measured by using BCA Protein Concentration Assay.

Hapten (32) is conjugated with KLH using a conjugation procedure similar to that described above.

Scheme 14

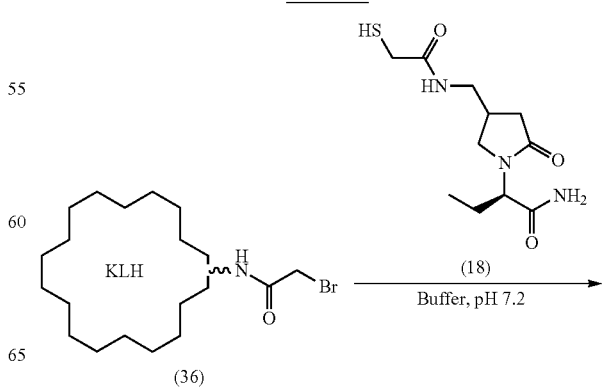

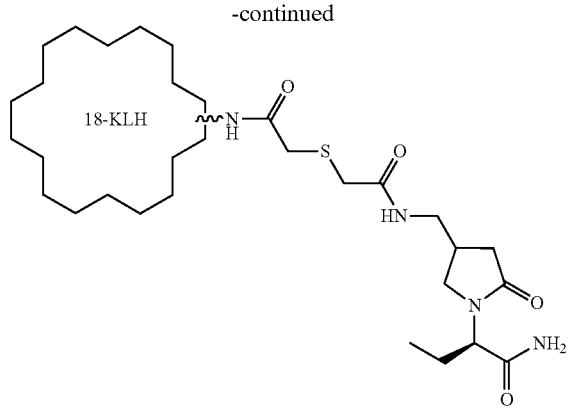

Example 15

Scheme 15 is a Schematic Representation of a Chemical Reaction for Converting G6PDH (35) into Bromoacetyl Glucose-6-Phosphate Dehydrogenase (37)

100 µL DMF was added to bromoacetic acid NHS (Sigma 3.06 mg, 12.97 µM) and stirred. A 2.0 mL (10 mg/mL) G6PDH solution was prepared in 0.025 M phosphate carbonate buffer, pH 7.2 and adjusted to pH 8.5 with 0.4 M carbonate buffer. 45 mg disodium G6P and 90 mg NADH, was dissolved in the G6PDH solution. Bromoacetic acid NHS was added to G6PDH solution at 5 µL increments. Enzyme activity was measured on the HITACHI 917 analyzer after each addition. Bromoacetic acid NHS was added until approximately 63.0% enzyme deactivation was obtained. G6PDH conjugation solution was dialyzed with 3×4 liter portions of 0.01 M phosphate, pH 7.2.

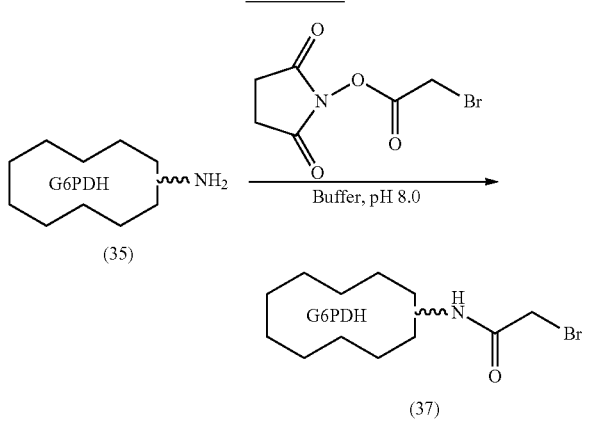

Example 16

Scheme 16 is a Schematic Representation of a Chemical Reaction for Converting a Levetiracetam (18) Analog into a Glucose-6-Phosphate Dehydrogenase Conjugate (18-G6PDH)

Bromoacetyl Glucose-6-Phosphate Dehydrogenase (37) is buffer exchanged with 50 mM phosphate-1.0 mM EDTA, pH 7.25. A solution of the protein is mixed with a dithioerythritol (25 mM final concentration in the phosphate-EDTA buffer) and mixture incubated at 4° C. for 16 hours. The protein solution is then buffer exchanged with 50 mM phosphate, 1.0 mM EDTA, 5 mM DTT, pH 7.25. The protein solution is mixed with 40 fold molar excess of a DMF solution of levetiracetam derivative (18) and reaction mixture is stirred gently at 4° C. for 16 to 24 hours. Excess (18) is separated from the enzyme-hapten conjugate by passing the reaction mixture over a column of Sephadex G 50 in 50 mM phosphate, pH 7.0. The column fractions containing the enzyme-hapten conjugate are pooled by measuring absorption at 280 nm which gave conjugate (18-G6PDH).

Hapten (32) is conjugated with G6PDH using a conjugation procedure similar to that described above.

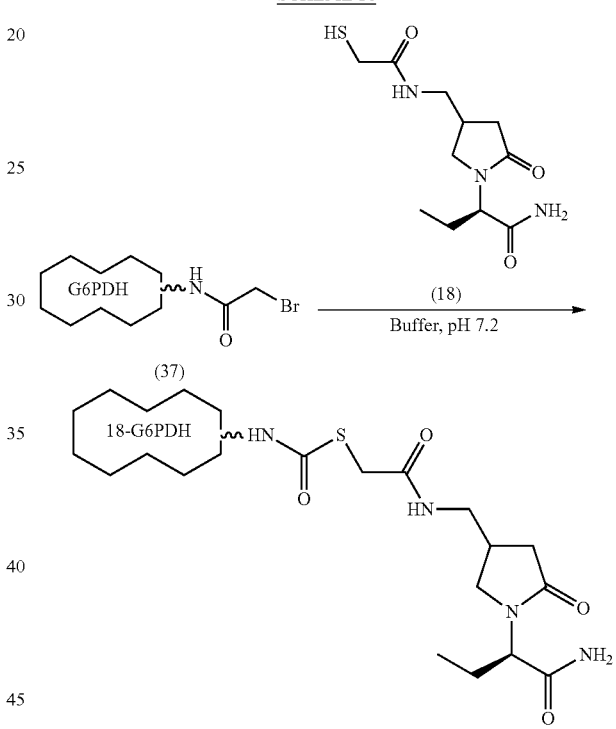

Example 17

Scheme 17 is a Schematic Representation of a Chemical Reaction for Converting a Levetiracetam (19) Analog into a Glucose-6-Phosphate Dehydrogenase Conjugate (19-G6PDH)

The levetiracetam derivative hapten (19) is designed for proteins containing cysteine groups such as mutant G6PDH or introduction of thiol-groups by chemical reactions. See, U.S. Pat. Nos. 6,455,288, 6,090,567, 6,033,890, which are incorporated by reference in their entireties. SH-G6PDH is buffer exchanged with 50 mM phosphate-1.0 mM EDTA, pH 7.25. A solution of the enzyme is mixed with a solution of dithioerythritol (0.5 M solution in the phosphate-EDTA buffer) and mixture is incubated at 4° C. for 16 hours. The protein solution is then buffer exchanged with 50 mM phosphate-1.0 mM EDTA-0.025 mM DTT, pH 7.25. Thiol content of the protein is determined by titration with a solution of dithiodipyridine, and is reported as thiols per mole of the protein. The protein solution is mixed with 40 fold molar excess of a DMF solution of hapten (19) and reaction mixture is stirred gently at 4° C. for 16-24 hours. Excess hapten (19) is separated from the enzyme-hapten conjugate by passing the reaction mixture over a column of Sephadex G 50 in 50 mM phosphate, pH 7.0. The column fractions containing the enzyme-hapten conjugate is pooled by measuring absorption at 280 nm to give conjugate (19-G6PDH).

Hapten (25) is conjugated with G6PDH using a conjugation procedure similar to that described above.

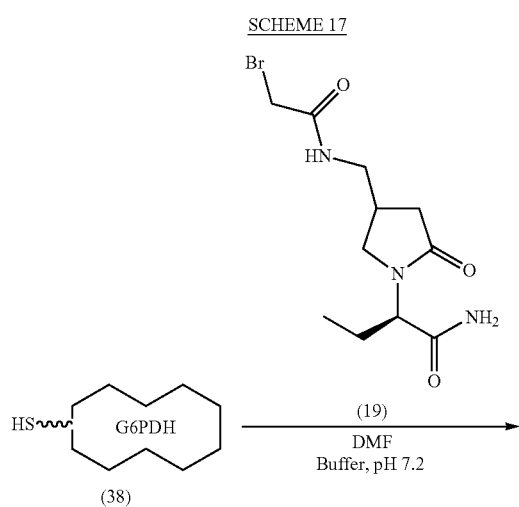

Example 18

Scheme 18 is a Schematic Representation of a Chemical Reaction for Converting a Levetiracetam (19) Analog into a KLH Immunogen (19-KLH)

The levetiracetam derivative hapten (19) is conjugated to proteins where thiol groups are chemically introduced. Commercially available linker, N-succinimidyl-S-acetylthioacetate (40) is reacted with primary amine of KLH (34), which adds protected sulfhydryls. Deprotection of protected sulfhydryls with hydroxyl amine produces a desired thiolated KLH (41). Conjugation of hapten (19) with thiolated KLH (41) results in immunogen (19-KLH).

Lyophilized KLH (Pierce) is reconstituted with phosphate buffer (0.1 M, 0.15 M NaCl, 1 mM EDTA, pH 8.0). The KLH (34) solution is transferred to a reaction vial. Immediately before reaction, N-Succinimidyl-S-acetylthioacetate (40, SATA) is dissolved in DMSO (results in ~55 mM solution). The SATA solution is combined with the protein solution. The contents are mixed and reaction mixture is incubated at room temperature for at least 30 minutes. A Sephadex G-50 column is equilibrated with two column volumes of buffer (0.1 M phosphate, 0.15 M NaCl, pH 7.2-7.5). The reaction mixture is applied to column. Fractions (500 µL) are collected immediately. The fractions that contain protein are identified by measuring absorbance at 280 nm. Protein fractions are pooled. Deacylation to generate a sulfhydryl for use in cross-linking is accomplished adding 1 deacetylation solution (0.5 M Hydroxylamine, 25 mM EDTA in PBS, pH 7.2-7.5). Contents are mixed and reaction mixture is incubated for 2 hours at room temperature. Sephadex G-50 desalting column is used to purify the sulfhydryl-modified protein from the hydroxylamine in the deacetylation solution. The pooled fractions are concentrated using Amicon concentrator.

Dithiothreitol (DTT, 1 mM) is added to thiolated KLH (28) to ensure reduction of disulfide bonds. The solution is allowed to mix overnight at 4° C. Bromoacetamido levetiracetam derivative hapten (19) is dissolved in 0.2 mL DMF. Levetiracetam derivative hapten (19) DMF solution is added in 5 to 10 µL quantities to a solution of thiolated KLH (41). The reaction is continued overnight at 4° C. This solution is dialyzed against three changes of HEPES buffer (10 mM, pH 7.0, 1 mM EDTA). This procedure yields immunogen (19-KLH).

Hapten (25) is conjugated with KLH using a conjugation procedure similar to that described above.

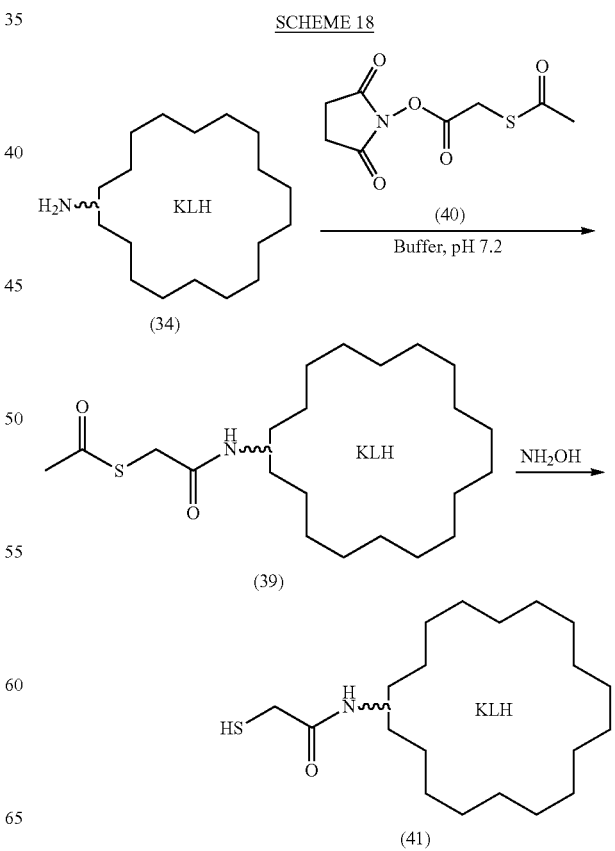

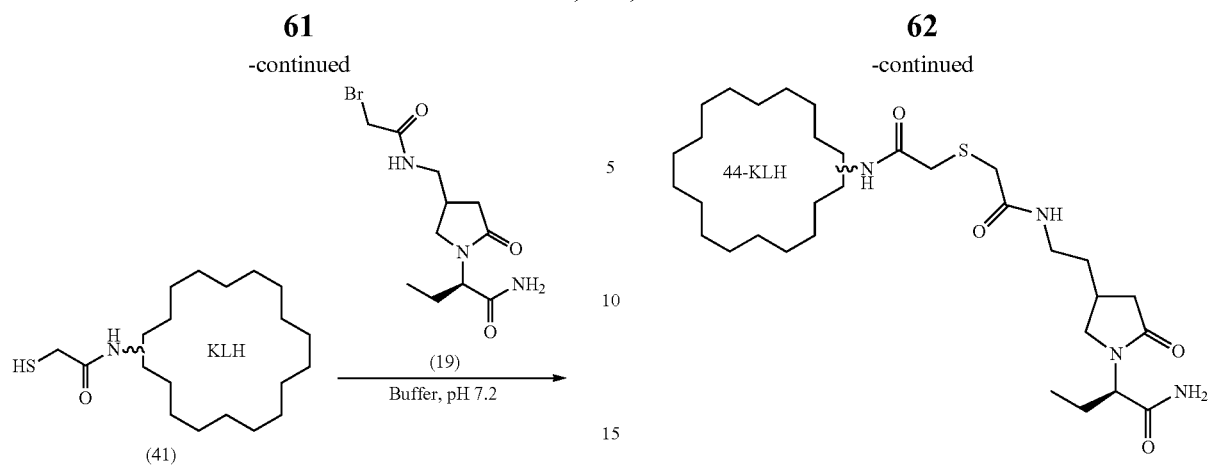
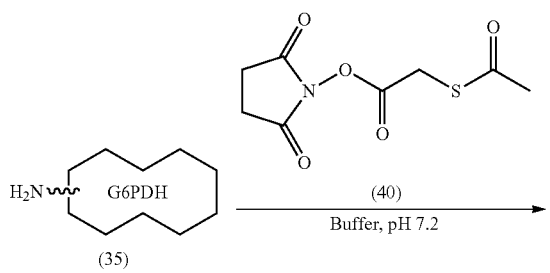
Example 20
Scheme 20 is a Schematic Representation of a Chemical Reaction for Converting a Levetiracetam (19) Analog into a G6PDH Conjugate (19-G6PDH)
Hapten (25) is conjugated with G6PDH using a conjugation procedure similar to that described in Example 19.
Example 19
KLH (41) was conjugated to hapten (44) as described in Example 18 above resulting in immunogen (44-KLH).
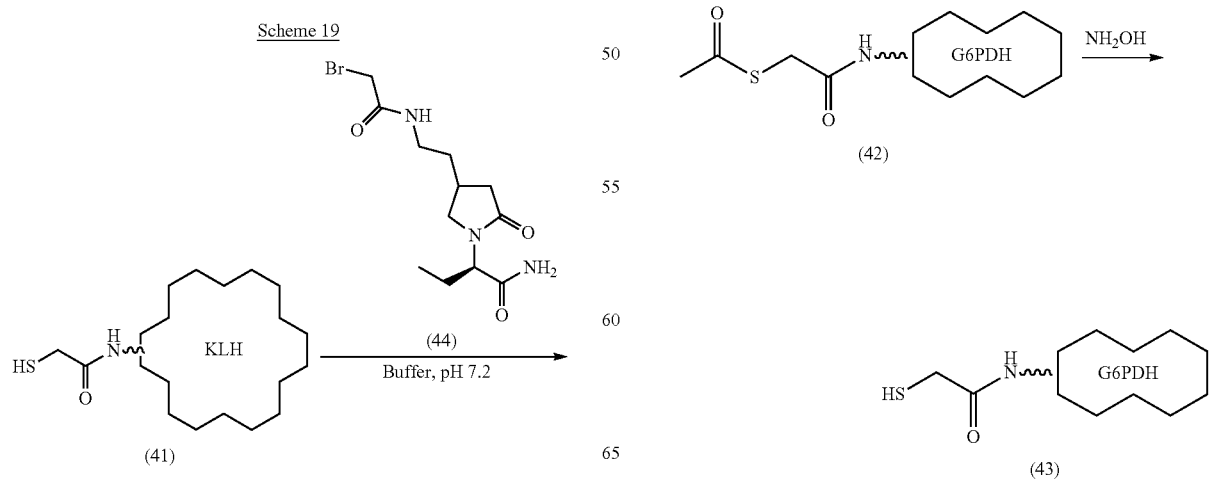

-continued

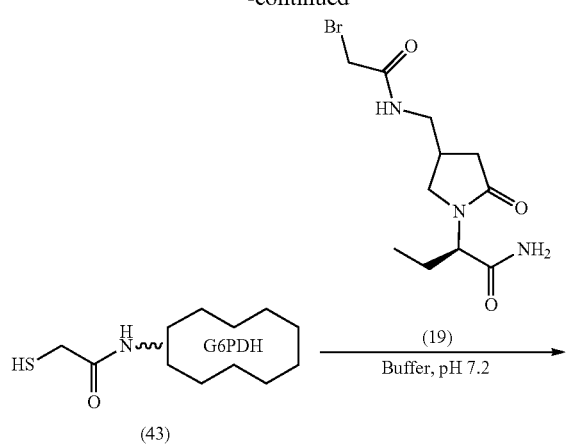

(43)

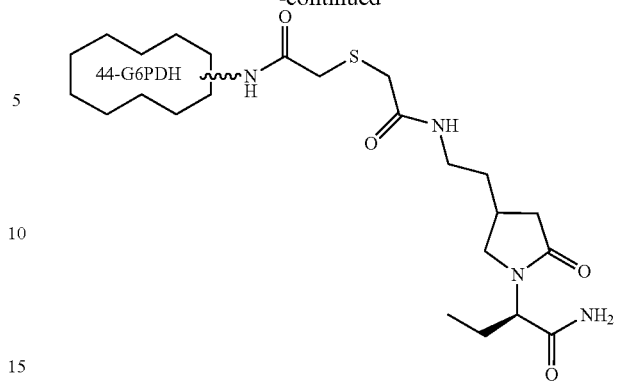

Example 21

G6PDH (43) was conjugated to hapten (44) as described in Example 20 above resulting in conjugate (44-G6PDH).

Scheme 21

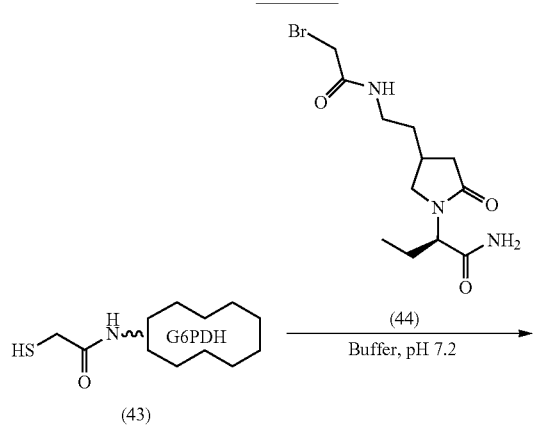

(43)

-continued

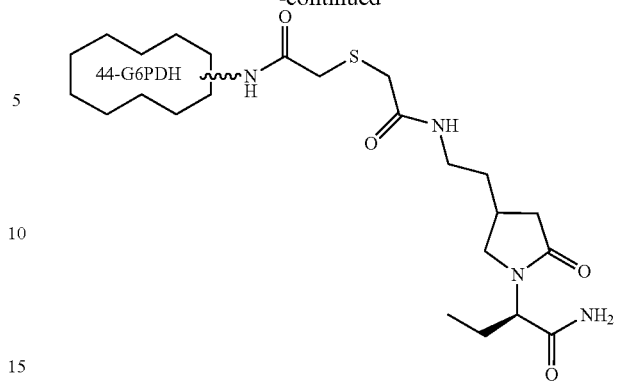

Example 22

Preparation of Levetiracetam Derivative Antibodies Reactive to Levetiracetam.

The levetiracetam antibodies and enzyme conjugates prepared as described in the above examples may be employed in assays for the detection of levetiracetam. Either of the immunogens can be injected into a mouse, sheep or rabbit to raise antibody. Polyclonal sera from κ live rabbits were prepared by injecting six animals with immunogen (44-KLH). This immunogenic formulation comprises 200 µg of the immunogen for the first immunization and 100 µg for all subsequent immunizations. Regardless of immunogen amount, the formulation was then diluted to 1 mL with sterile saline solution. This solution was then mixed thoroughly with 1 mL of the appropriate adjuvant: Freund's Complete Adjuvant for first immunization or Freund's Incomplete Adjuvant for subsequent immunizations. The stable emulsion was subsequently injected subcutaneously with a 19×1½ needle into New Zealand white rabbits. Injections were made at 3-4 week intervals. Bleeds of the immunized rabbits were taken from the central ear artery using a 19×1 needle. Blood was left to clot at 37° C. overnight, at which point the serum was poured off and centrifuged. Finally, preservatives were added in order to form the polyclonal antibody material. Rabbit polyclonal antibodies to levetiracetam produced by the above procedure immunized with immunogen (44-KLH) are designated as #12019, #12020, #12021, #12022, #12023, and #12024. Rabbit polyclonal antibody #12019 is used in examples below.

Rabbit polyclonal antibody #12019-P8 was used to measure a substantial change in enzyme activity, generate a calibration curve, and evaluate assay precision, accuracy and specificity. The antibody was added into the antibody diluent to prepare the antibody reagent. The antibody reagent consists of antibody as prepared above, buffer, stabilizers, preservatives, and the substrates for the enzyme conjugate nicotinamide adenine dinucleotide (NAM and glucose-6-phosphate. Enzyme conjugate comprising compound (44-G6PDH) G6PDH was added into the conjugate reagent to prepare the enzyme conjugate reagent. The enzyme conjugate reagent comprises the conjugate, buffer, stabilizers and preservatives. Enzyme conjugate (44-G6PDH) was used with rabbit polyclonal antibody #12019-P8 in examples below. This technique is generally applicable to produce polyclonal antibodies to levetiracetam derivatives and assess their utility.

Monoclonal antibodies may be prepared using standard hybridoma procedures as described in detail (Kohler, G. et al., *Nature* 256: 495-497 (1976); Hurrell, *Monoclonal Hybridoma Antibodies: Techniques and Applications*, CRC Press, Boca Raton, Fla. (1982)). This hybridoma technique is generally applicable to produce monoclonal antibodies to the levetiracetam derivatives.

Example 23

Roche HITACHI 917 Clinical Chemistry Analyzer.

The levetiracetam derivative antibodies and enzyme conjugates may be advantageously used in a homogeneous assay format to detect levetiracetam in samples. An enzyme immunoassay or ARK Assay, which is a homogeneous enzyme immunoassay experiment, was performed to test antibodies prepared as described in Example 22. The ARK Assay for levetiracetam was conducted using a liquid, ready-to-use, two-reagent kit. A clinical chemistry analyzer useful to set up the assay is HITACHI 917. The HITACHI 917 is an automated biochemistry analyzer used by medical laboratories to process biological fluid specimens, such as urine, cerebrospinal fluid, and most commonly, blood. Manufactured by Boehringer Mannheim, the HITACHI 917 is a commonly used routine chemical chemistry.

Figure 2A:
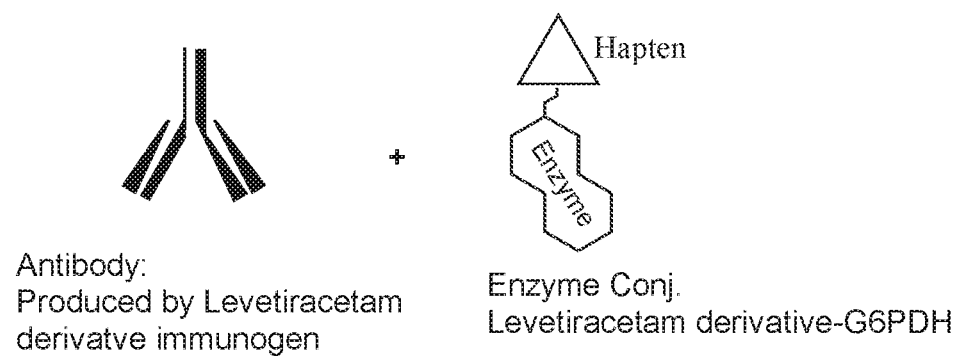
FIGS. 2A and 2B are flow diagrams illustrating embodiments of a method for performing an immunodiagnostic assay for levetiracetam. The rate of increasing absorbance at 340 nm due to the conversion of NAD+(Nicotinamide adenine dinucleotide reduced) to NADH (Nicotinamide adenine dinucleotide oxidized) is related to the concentration of levetiracetam in the sample by a mathematical function. The enzyme reaction is catalyzed by levetiracetam-G6PDH (Glucose-6-phosphate dehydrogenase) conjugate.
Figure 2A:
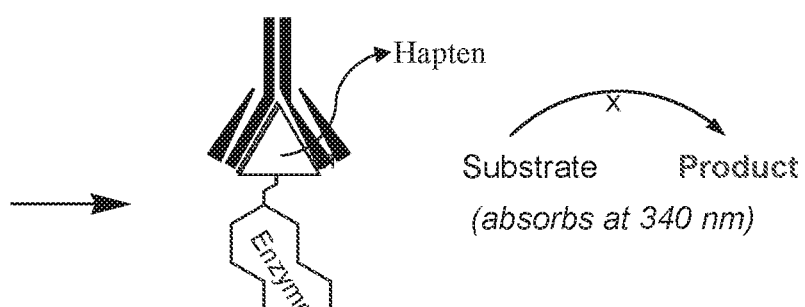
Figure 2B:
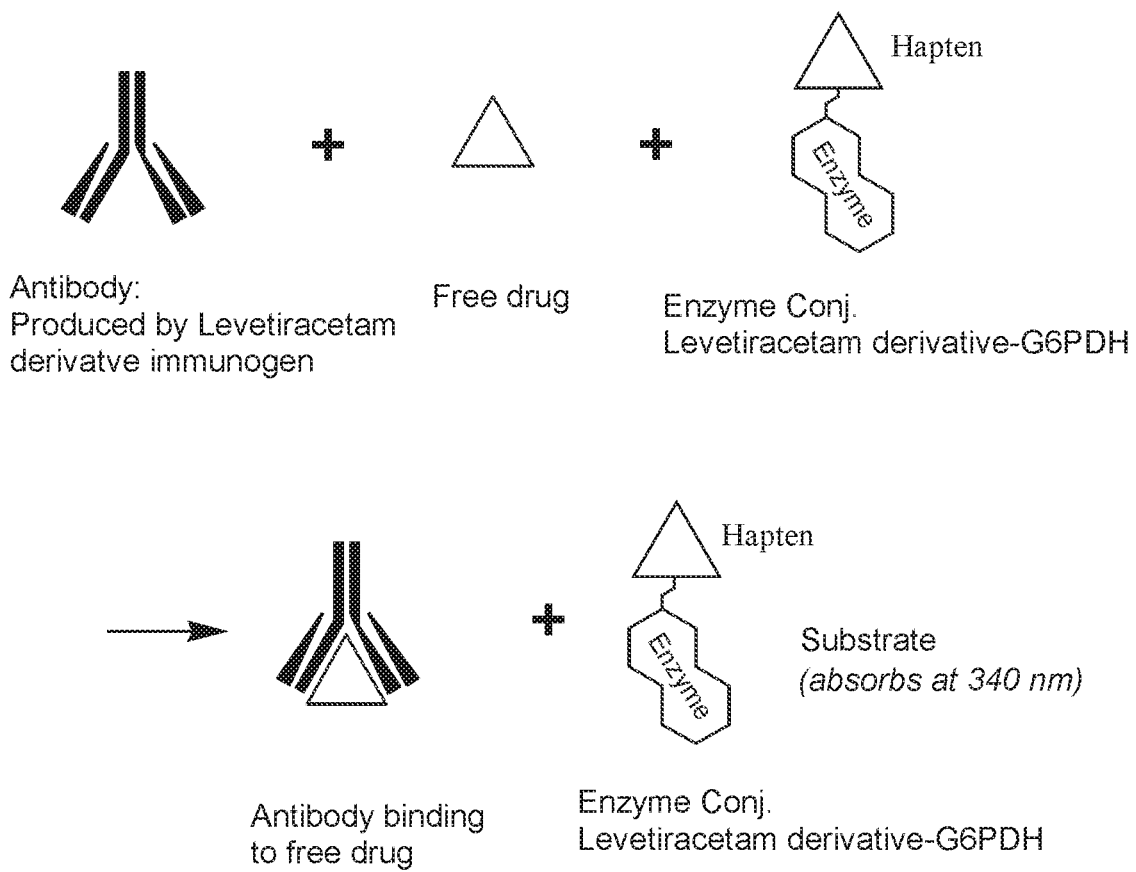

Levetiracetam containing sample was incubated with antibody reagent followed by the addition of the enzyme conjugate reagent. The enzyme conjugate activity decreases upon binding to the antibody. As illustrated in FIGS. 2A and 2B, the enzyme conjugate, which is not bound to the antibody, catalyzes the oxidation of glucose 6-phosphate (G6P). The oxidation of G6P is coupled with the reduction of $NAD^+$ to NADH, which was measured at 340 nm. The change in the absorbance at 340 nm was measured spectrophotometrically. The levetiracetam concentration in a specimen was measured in terms of G6PDH activity. The increase in the rate at 340 nm was due to the formation of NADH and is proportional to the enzyme conjugate activity. An assay calibration curve was generated using levetiracetam spiked into negative calibrator matrix. The assay rate increases with increasing the concentration of drug in the sample.

Example 24

Calibration Curve

Figure 3:
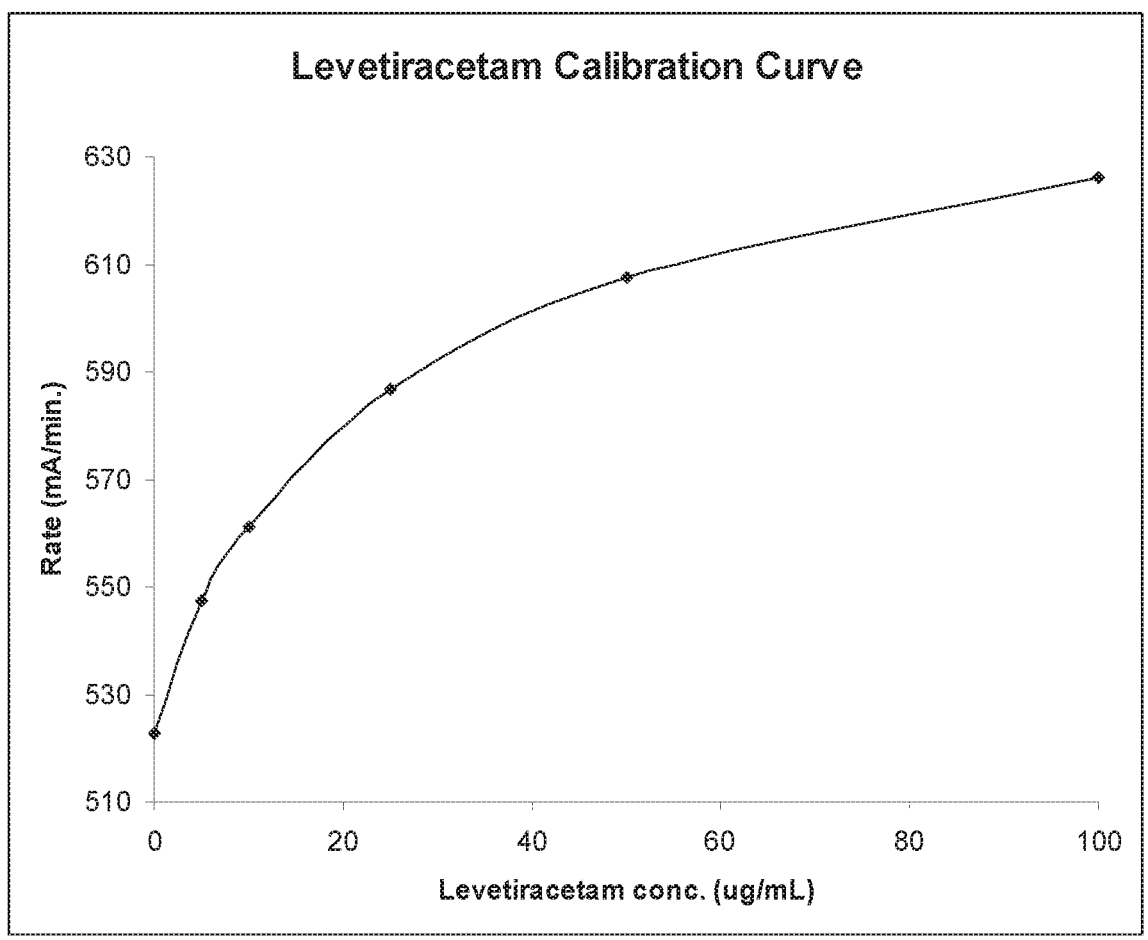
FIG. 3 shows a typical calibration curve for a competitive homogeneous immunoassay for levetiracetam in pooled human serum calibrator matrix using a Roche Hitachi 917 analyzer.
Figure 4:
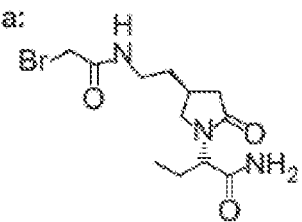
FIG. 4 shows a mass spectrograph of Compound 44.
Figure 4:
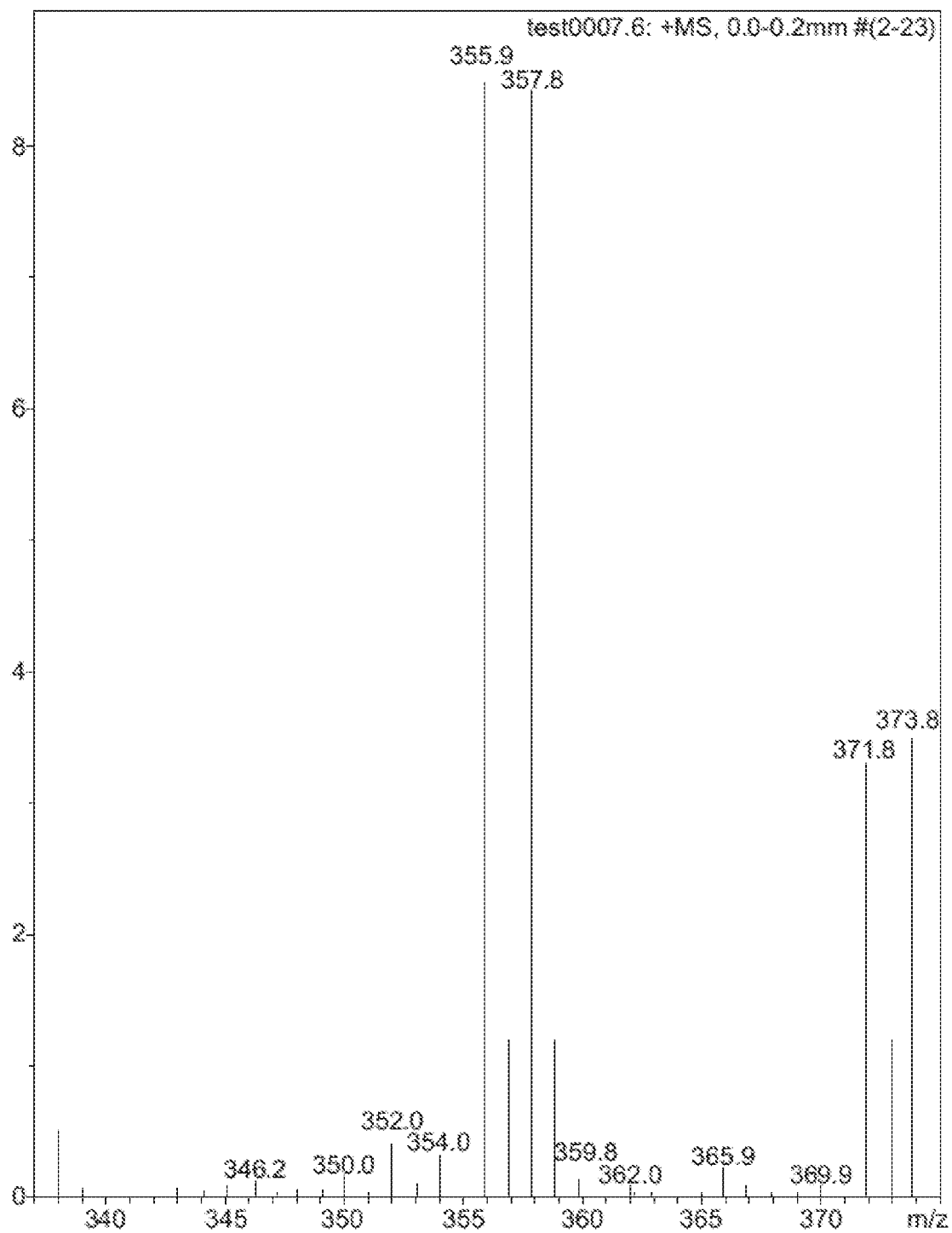
Figure 5:
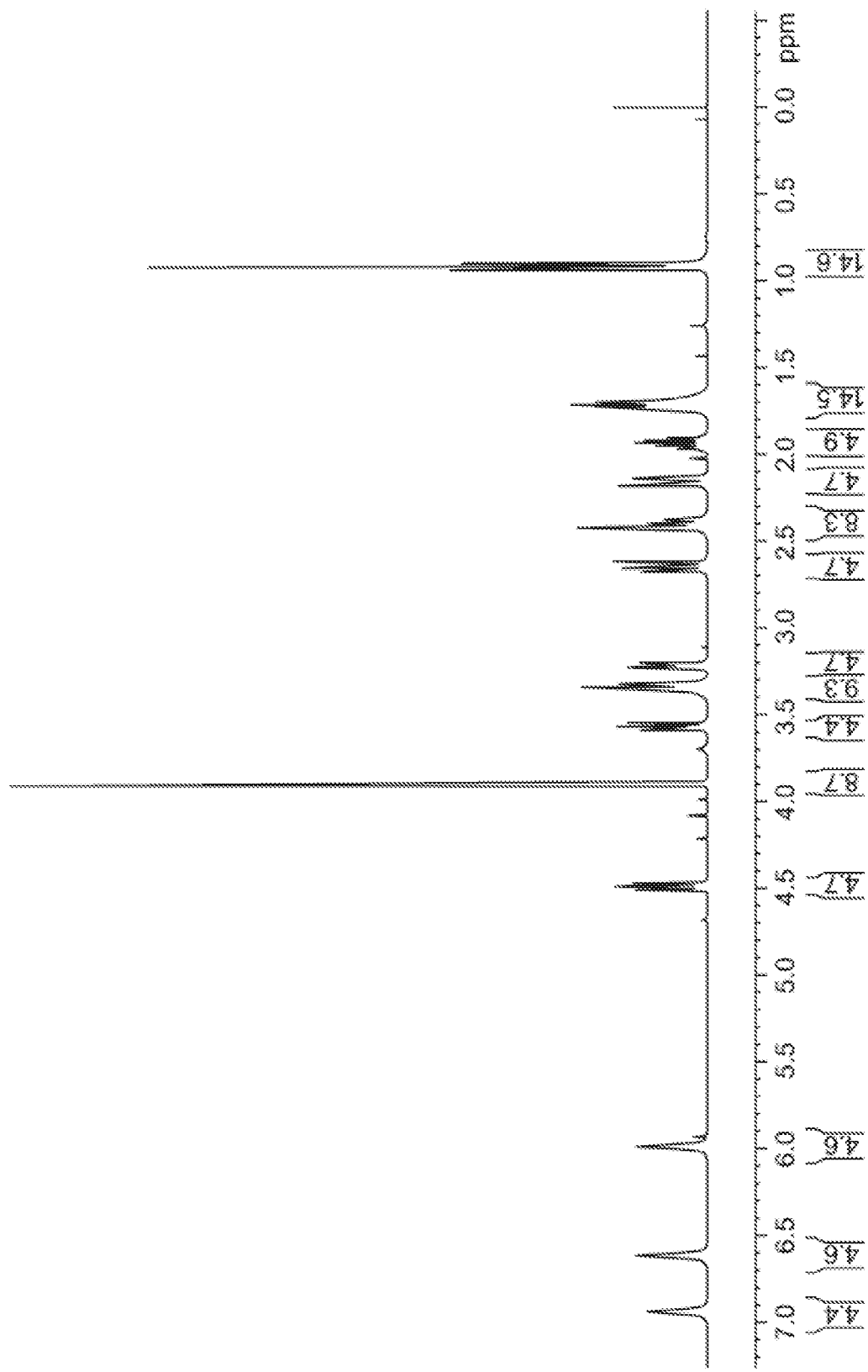
FIG. 5 shows a ¹H NMR spectrum of Compound 44.

Levetiracetam was dissolved in methanol to give a stock solution of 1000 μg/mL. Pooled human serum was aliquoted in 10 mL portions. Levetiracetam stock solution was added to the aliquots of human serum in preparing a series of known concentrations of levetiracetam calibrators ranging from 0 to 100 μg/mL. Similarly, Quality Control samples were prepared (15.0, 35.0 and 75.0 μg/mL). The antibody/substrate reagent #11341P4-6-Ab containing antibody ##12019-P8 was assayed with enzyme reagent #110607-D63-E containing conjugate (44-G6PDH). Calibration curves were generated on the HITACHI 917 automated clinical chemistry analyzer, as described in Example 23 by assaying each level in duplicate. An example of these calibrator rates is shown in Table 2 and the graph is shown in FIG. 3.

TABLE 2

| Calibrator Reaction Rate | |
|---|---|
| Levetiracetam Conc. (μg/mL) | Reaction Rate (mA/min) Average of Duplicates |
| 0.0 | 522.6 |
| 5.0 | 547.4 |
| 10.0 | 561.2 |
| 25.0 | 586.9 |
| 50.0 | 607.5 |
| 100.0 | 626.0 |

Example 25

Accuracy of the Measurement.

Three levetiracetam Quality Control samples were prepared as described in Example 24 to give concentrations of levetiracetam of 15.0, 35.0 and 75.0 μg/mL. Enzyme Conjugate Reagent #110607-D63-E containing conjugate (44-G6PDH) and Antibody Reagent #11341P4-6-Ab containing antibody ##12019-P8 was used to generate precision data shown in Table 3. The accuracy data were derived from 2 runs on the same day. Each run for generating a calibration curve includes 10 replicates of each QC level per run with a total of 20 replicates from 2 runs. Quantification was performed on the HITACHI 917 analyzer as described in Example 23. Also, the accuracy of the measurement was calculated as a percentage of the nominal value of the QC samples (Table 3).

TABLE 3

| | | Precision | |
|---|---|---|---|
| N | QC Conc. (μg/mL) | Mean (μg/mL ± SD) | Accuracy (%) |
| 10 | 15.0 | 14.88 ± 1.02 | 99.21 |
| 10 | 35.0 | 35.77 ± 2.85 | 102.19 |
| 10 | 75.0 | 77.16 ± 4.48 | 102.88 |

Example 26

Specificity of the Immunoassay in the Presence of 2-Pyrrolidone-N-Butyric Acid, a Levetiracetam Metabolite (FIGS. 1(1) and 1(2)).

The major metabolic pathway of levetiracetam (24% of dose) is an enzymatic hydrolysis of the acetamide group. The metabolites have no known pharmacological activity and are renally excreted. To human serum negative for levetiracetam was added levetiracetam dissolved in methanol to achieve a concentration of concentration of 30 μg/mL of levetiracetam (FIG. 1(1)). To a second sample was added 2-pyrrolidone-N-butyric acid dissolved in methanol to achieve a concentration of 150.0 μg/mL 2-pyrrolidone-N-butyric acid (FIG. 1(2)). To a third sample was added 30 μg/mL of levetiracetam plus 406.4 μg/mL 2-pyrrolidone-N-butyric acid (FIG. 1(2)). The samples were assayed on the HITACHI 917. The levetiracetam metabolite, 2-pyrrolidone-N-butyric acid was tested in the immunoassay for potential crossreactivity with Enzyme Conjugate Reagent #110607-D63-E containing conjugate (44-G6PDH) and Antibody Reagent #11341P4-6-Ab containing antibody #12019-P8. As shown in Table 5, antibody #12019-P8 does not cross-react with 2-pyrrolidone-N-butyric acid metabolite, indicating a highly specific antibody was produced.

TABLE 5

Crossreactivity to Levetiracetam Metabolites

High level of 2-pyrrolidone-N-butyric acid was tested. % Crossreactivity = 100 × ("apparent concentration of levetiracetam"/"concentration of crossreactant")

| Compound | Concentration Tested (µg/ml) | Levetiracetam Result (µg/mL) | % Cross Reactivity |
|---|---|---|---|
| Levetiracetam | 30.0 | 29.9 | 100 |
| 2-pyrrolidone-N-butyric acid | 150.0 | 0 | 0 |
| 2-pyrrolidone-N-butyric acid | 406.4 | 0 | 0 |

The preceding merely illustrates the principles of the embodiments of the present invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

What is claimed is:

1. A compound of the formula:

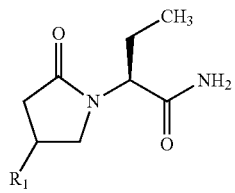

wherein
  $R_1$ is selected from the group consisting of —(CH$_2$)$_n$—NH—C(O)—(CH$_2$)$_n$—C(O)—Z and —(CH$_2$)$_n$—NH—C(O)—(CH$_2$)$_n$—S—(CH$_2$)$_n$—C(O)—Z,
    wherein each n is an integer from 1 to 10; and
  Z is selected from the group consisting of an immunogenic carrier and a fluorophore, and
acid salts thereof.

2. The compound of claim 1, wherein Z is the immunogenic carrier.

3. The compound of claim 2, wherein the immunogenic carrier is bovine serum albumin (BSA) or keyhole limpet hemocyanin (KLH).

4. The compound of claim 2, wherein the immunogenic carrier is selected from the group consisting of hemocyanins, globulins, albumins, and polysaccharides.

5. The compound of claim 2, wherein the immunogenic carrier is selected from the group consisting of a protein, a peptide, a glycoprotein, a saccharide, a nucleic acid and a polynucleotide.

6. The compound of claim 2, wherein the immunogenic carrier is KLH.

7. The compound of claim 1, wherein $R_1$ is —(CH$_2$)$_n$—NH—C(O)—(CH$_2$)$_n$—C(O)—Z.

8. The compound of claim 7, wherein the compound is of the formula:

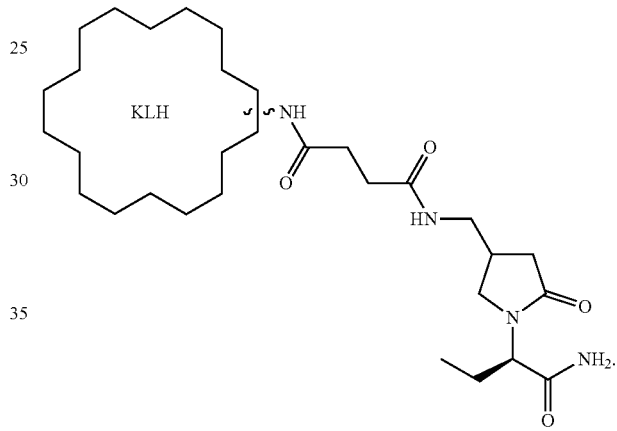

9. The compound of claim 1, wherein $R_1$ is —(CH$_2$)$_n$—NH—C(O)—(CH$_2$)$_n$—S—(CH$_2$)$_n$—C(O)—Z.

10. The compound of claim 9, wherein the compound is of the formula:

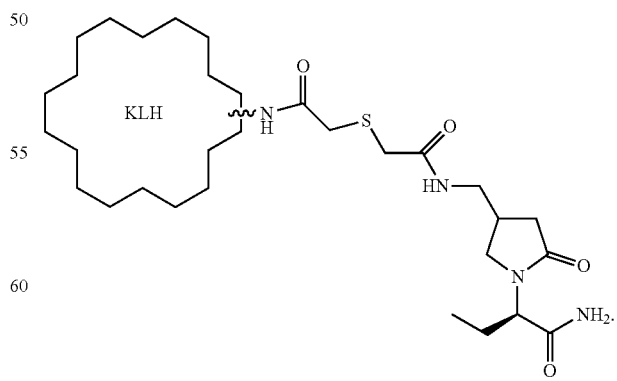

11. The compound of claim 9, wherein the compound is of the formula:

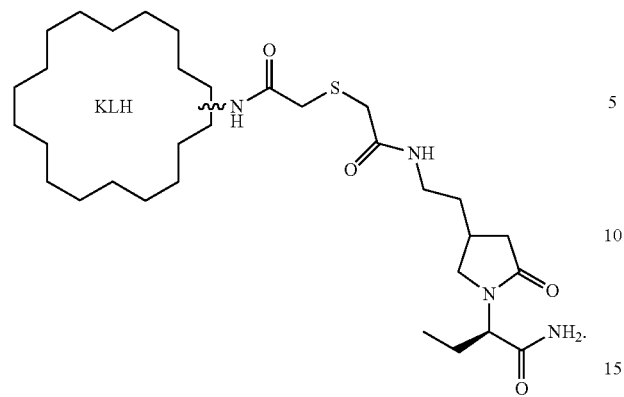
* * * * *